United States Patent
Bierbach et al.

(10) Patent No.: US 11,591,357 B2
(45) Date of Patent: Feb. 28, 2023

(54) PAYLOAD AND LINKER DESIGNS FOR PLATINUM-ACRIDINE ANTICANCER AGENTS AND METHODS THEREOF

(71) Applicant: Wake Forest University, Winston-Salem, NC (US)

(72) Inventors: Ulrich Bierbach, Winston-Salem, NC (US); Xiyuan Yao, Winston-Salem, NC (US); Hanwen Wang, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 170 days.

(21) Appl. No.: 16/642,074

(22) PCT Filed: Aug. 28, 2018

(86) PCT No.: PCT/US2018/048309
§ 371 (c)(1),
(2) Date: Feb. 26, 2020

(87) PCT Pub. No.: WO2019/046278
PCT Pub. Date: Mar. 7, 2019

(65) Prior Publication Data
US 2020/0181185 A1  Jun. 11, 2020

Related U.S. Application Data

(60) Provisional application No. 62/550,817, filed on Aug. 28, 2017.

(51) Int. Cl.
*C07F 15/00* (2006.01)
*A61K 47/51* (2017.01)

(52) U.S. Cl.
CPC .......... *C07F 15/0093* (2013.01); *A61K 47/51* (2017.08)

(58) Field of Classification Search
CPC .................................................... C07F 15/0093
See application file for complete search history.

(56) References Cited

PUBLICATIONS

Qiao (J Biol Inorg Chem. Mar. 2014 ; 19(3): 415-426. doi:10.1007/s00775-013-1086-1). (Year: 2014).*
Qiao et al. "Investigating the cellular fate of a DNA-tergeted platinum-based anticancer agent by orthogonal double-click chemistry", J Bio Inorg Chem, 2014, vol. 19(3), pp. 415-426.
Wilson et al. "Synthetic Methods for the Preparation of Platinum Anticancer Complexes", Chem Rev, 2014, vol. 114 (8), pp. 4470-4495.
Ding et al. "Using Fluorescent Post-Labeling to Probe the Subcellular Localization of DNA-Targeted Platinum", Angew Chem Int Ed Engl, 2013, vol. 52(12), 8 pages.
Wilson et al. "Modulation of Ligand Fluorescence by the Pt(II)/Pt(IV) Redox Couple", Inorganica Chim Acta, 2012, vol. 389, pp. 77-84.

* cited by examiner

*Primary Examiner* — Benjamin J Packard
(74) *Attorney, Agent, or Firm* — Fox Rothschild LLP

(57) ABSTRACT

The present invention relates to payloads containing functionalized platinum-(benz)acridine hybrid agents as cytotoxic warheads and a method of synthesizing the payloads. The payload can be regioselectively conjugated to a biologically active moiety in order to facilitate the delivery and/or enhance the activity of the platinum compound.

23 Claims, 3 Drawing Sheets

PAYLOAD AND LINKER DESIGNS FOR PLATINUM-ACRIDINE ANTICANCER AGENTS AND METHODS THEREOF

CROSS-REFERENCE TO RELATED APPLICATIONS

This application claims priority under 35 U.S.C. § 119(e) to U.S. Provisional Patent Application No. 62/550,817, filed Aug. 28, 2017, which is incorporated herein by reference.

FIELD OF THE INVENTION

The present invention relates to functionalized forms of highly cytotoxic platinum-acridine anticancer agents, which can be introduced as payloads in carriers, such as cancer-targeted peptides, plasma proteins, synthetic polymers, and nanomaterials.

BACKGROUND OF THE INVENTION

Platinum anticancer agents such as cisplatin, carboplatin and oxaliplatin presently in clinical use are among the most widely used anticancer agents in the world. In particular, these platinum drugs have been known to exhibit superior antitumor activities against genital cancers such as testicular, ovarian, and bladder cancers as well as colorectal cancer.

However, like other low molecular weight anticancer agents such as paclitaxel, doxorubicin, etc., platinum anticancer agents administered systemically attack not only tumor cells and tissues but also normal cells and tissues equally without tumor selectivity, which cause severe toxicities such as nephrotoxicity, neurotoxicity, etc. In addition, their acquired cross-resistance and low water-solubility seriously limit their utility for cancer treatment.

Tremendous efforts have recently been made worldwide for the development of tumor targeting anticancer agents having selective cytotoxicity only on tumor cells or tissues, thereby drastically reducing adverse effects resulting from toxicity and overcoming drug-resistance. One of the most rational approaches to overcome non-selectivity and drug resistance inherently associated with the low molecular weight anticancer agents currently in clinical use is to use polymeric drug delivery systems, which have been intensively studied for the last decade. As representative examples, there are two different methods (nano-delivery and molecularly targeted delivery) to afford the low molecular weight anticancer agents to have tumor selectivity.

However, the efficacy and bioavailability of many of such conjugate drugs remain questionable. Further, the biocompatibility, tumor selectivity, and efficacy are yet to be improved.

Therefore, a need exists to develop more effective and selective anticancer agents with enhanced bioavailability and efficacy.

SUMMARY OF THE INVENTION

The present invention provides an oncology toolbox for personalized cancer therapy. This invention addresses the above-mentioned need by providing design strategies and chemical methodology that allow extending suitably functionalized platinum-acridines with synthetic-organic linkers. Linker designs and synthetic pathways are reported that are uniquely compatible with the chemical requirements of platinum-acridine cytotoxic warheads. The resulting linker-warhead constructs can be introduced as payloads in carriers, such as monoclonal antibodies (mAbs) (in antibody-drug conjugates, ADCs) and other cancer-targeted peptides, plasma proteins, synthetic polymers, and nanomaterials.

As a result of the conjugation with suitable carriers such as an mAb, conventional anticancer agents acquire strong affinity to receptors or antigens preferentially expressed in tumor cells or tissues. Further, the coupling of a conventional anticancer agent with a suitable polymer and peptide can also improve the pharmacological profile such as solubility, circulation times, bioavailability, and enhanced permeability and retention (EPR) effect in tumor tissues.

Triggered release mechanisms of an anticancer agent from the payload include for example enzymatic dipeptide cleavage, pH-sensitive cleavage, platinum-mediated hydrolytic ester cleavage, and self-immolative linker degradation. In some of the illustrated embodiments, the payloads contain thiol-reactive, terminal maleimide groups suitable for conventional Michael adduct formation with cysteine residues. However, the maleimide (MAL) moiety can be replaced with other functional groups which will allow payload attachment to alternative residues, such as unnatural amino acids in engineered monoclonal antibodies.

An aspect of this disclosure provides a payload of the following formula: E-A-F. F is a functionalized platinum-acridine agent. E is a linker. A is a linkage group between E and F.

The functionalized platinum-acridine agent F can be further represented with the following general Formula I:

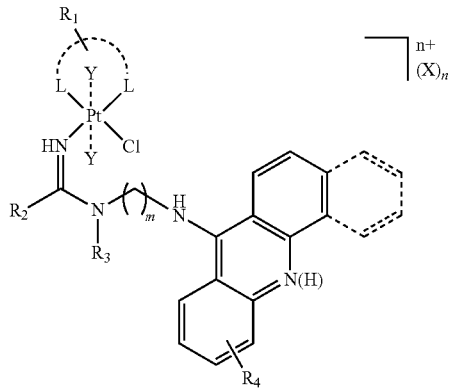

wherein $R_1$ represents an optional substituent of L and is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, (mono-, di-, or trihalogeno)methyl, or $C_{1-10}$ alkoxy;

$R_2$ and $R_3$ each independently represents a $C_{1-10}$alkyl, wherein the $C_{1-10}$alkyl is optionally (a) interpreted with one or more structural moieties selected from the group consisting of amino, oxygen, sulfur, amide, ester, carbamate, sulfonamide, sulfonyl, carbonate, ketone, disulfide, $(CH_2CH_2O)_p$ wherein p is an integer of 1 to 10, aryl or 5 to 12 membered aromatic or non-aromatic heterocyclic group; or (b) substituted with one or more structural moieties selected from the group consisting of hydroxy, imino, oxo, cyano, $C_{1-10}$ alkoxy, $C_{1-10}$ alkylthio, $C_{1-6}$alkylsulfonyl, di-$C_{1-10}$alkylamine, aryl or 5 to 12 membered aromatic or non-aromatic heterocyclic group;

$R_4$ is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, or (mono-, di-, or trihalogeno)methyl;

each L represents monodentate $NH_3$, or primary, secondary, tertiary amine or diamine wherein the nitrogen coordinates to Pt, further wherein the two amine ligands optionally link up to form a diamine/chelate;

X is nitrate or halide;

Y is an optional ligand, wherein when Y is present, Pt is Pt(IV), and when Y is void, Pt is Pt(II);

A is a linkage comprising one or more structural moieties selected from the group consisting of ester, amide, amino, carbamate, hydrazide, triazole, and disulfide, and A links E to one of $R_2$ and $R_3$;

E is a linker comprising a free terminal functional group capable of forming an amide, a thio-ether, or a triazole moiety;

m is 1, 2, 3, 4, 5 or 5; and n is 1, 2, 3 or 4.

Another aspect of the invention provides a conjugate of a biologically active moiety and the compound of Formula I described herein. In some embodiments, the conjugate contains an amide, thioether, or triazole linkage derived from the free terminal functional group of E.

Another aspect of the invention provides a method of improving the efficacy and/or bioavailability of the compound of Formula I or the cytotoxicity effect of the Pt warhead of the compound, comprising contacting the compound with a protein carrier, whereby the terminal functional group of the compound forms an amide or a thioether linkage with a nucleophilic group of the protein carrier.

Another aspect of the invention provides a method of conjugating a biologically active moiety with the compound of formula I, comprising reacting the terminal functional group of E with a counterpart functional group of the biologically active moiety.

Another aspect of the invention provides a method of treating cancer, comprising administering to a subject in need a therapeutically effective amount of the compound of formula I or the conjugate of the compound with a biologically active moiety.

DETAILED DESCRIPTION OF THE INVENTION

Figure 1:
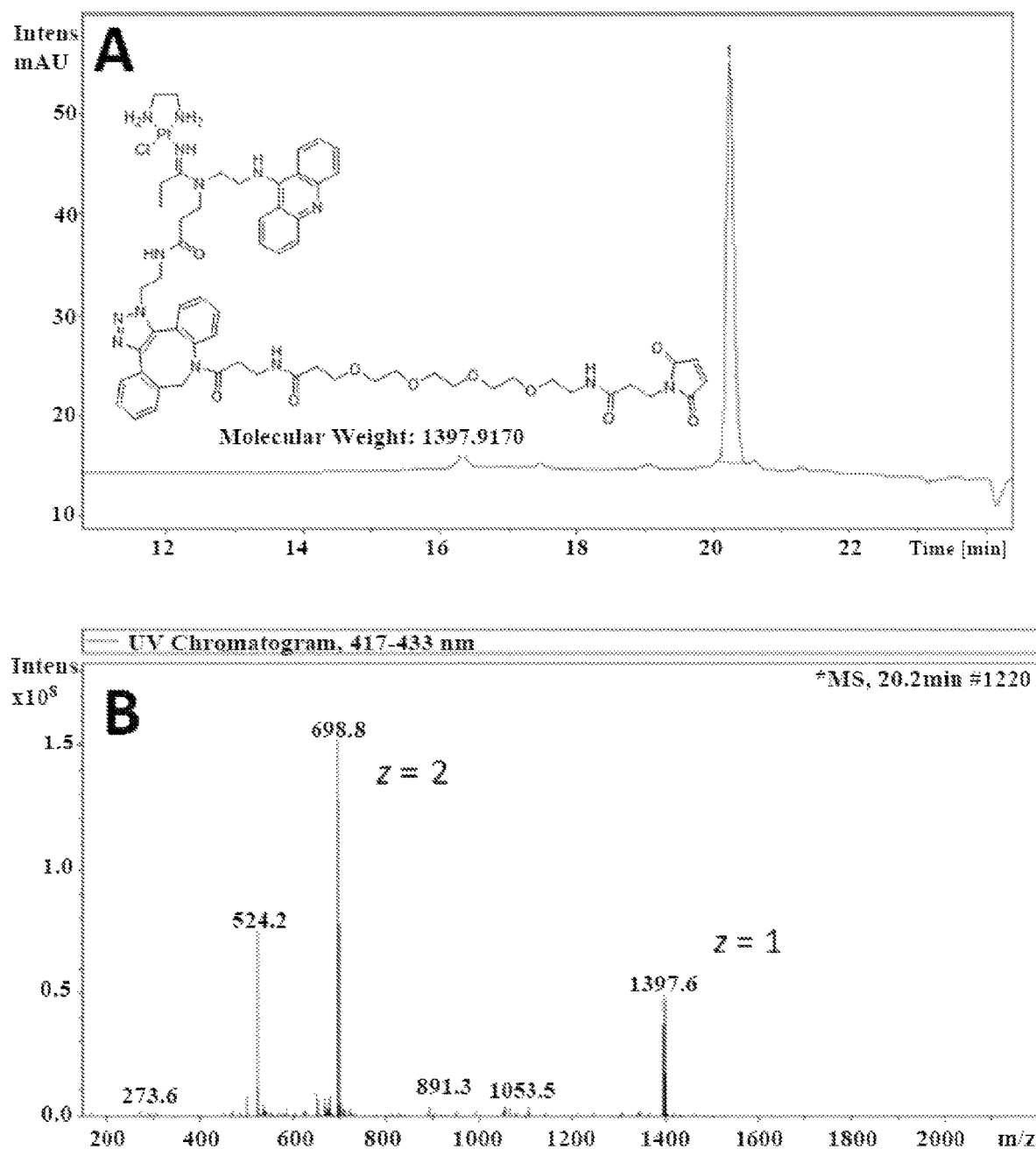
FIG. 1 shows the characterization of the prepared payload. (A) and (B): Characterization (LC-ESI-MS) of platinum-acridine payload PL2 containing terminal maleimide.
Figure 2:
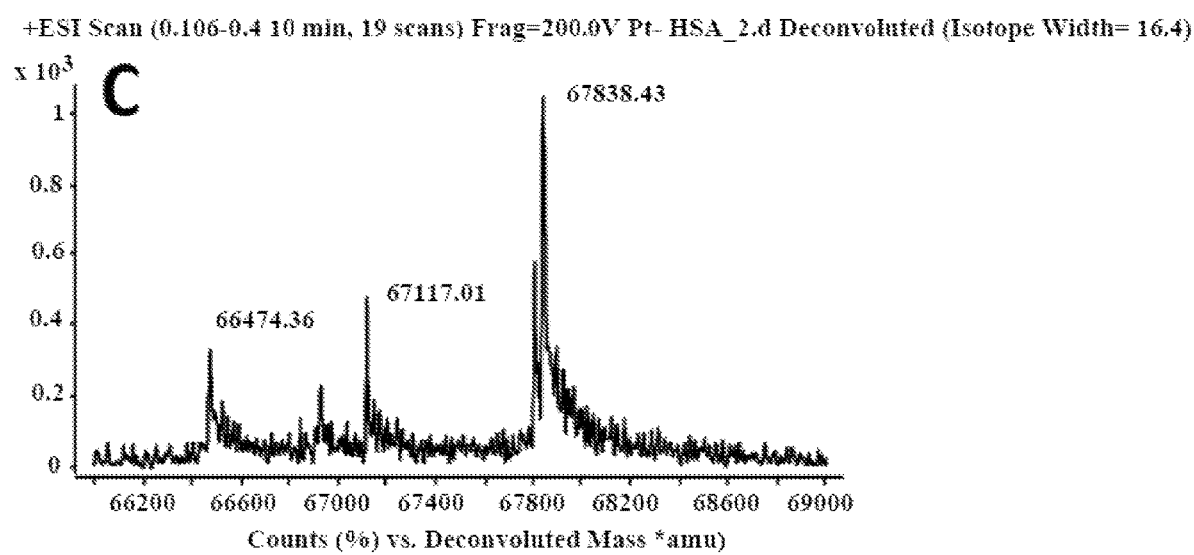
FIG. 2 shows ESI-ToF MS of payload-conjugated human serum albumin (HSA) derived from PL2.
Figure 3:
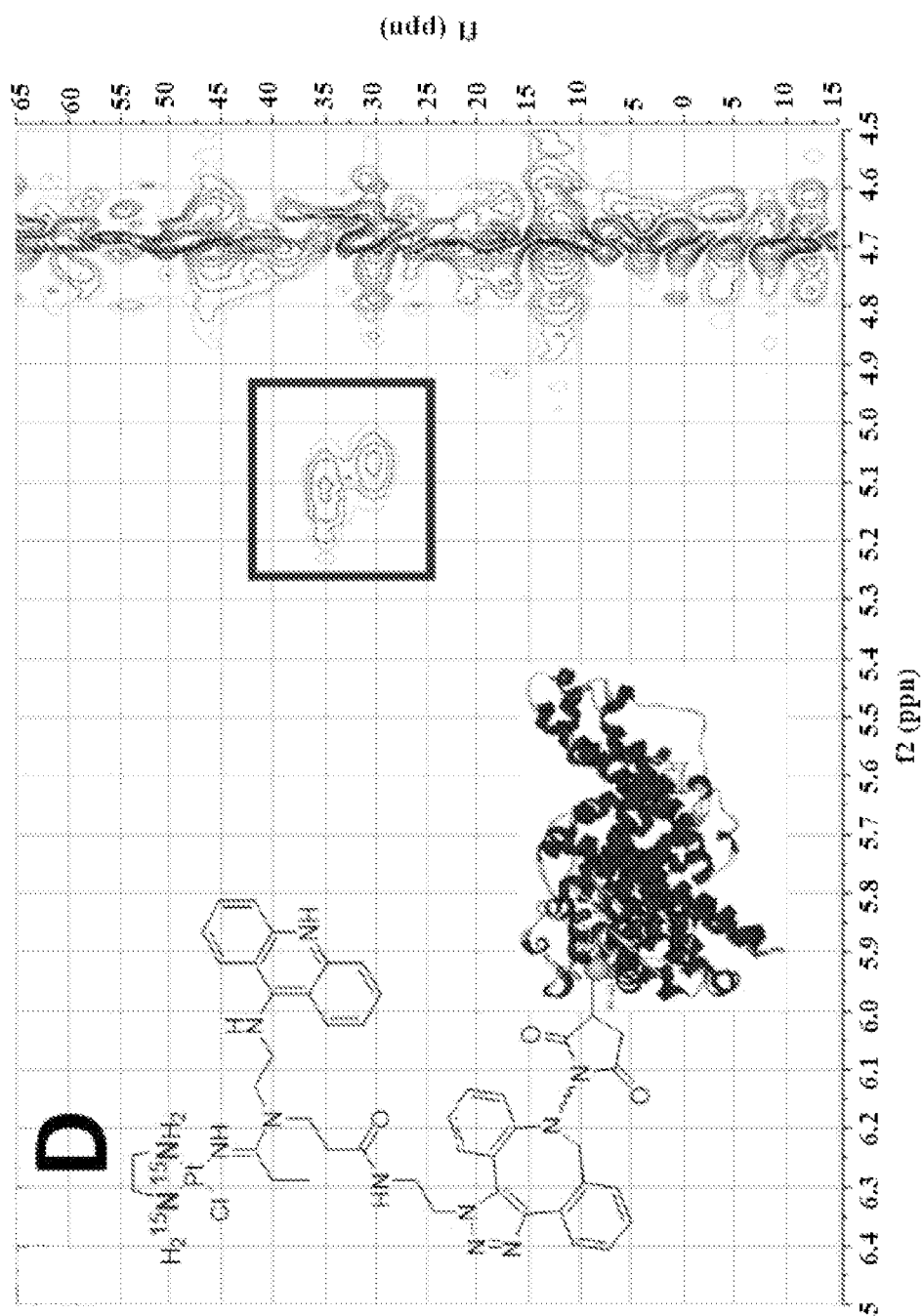
FIG. 3 shows that $^1H$-$^{15}N$ HSQC 2-D NMR (600 MHz) of $^{15}N$-labeled payload (here PL1) is conveniently used to confirm warhead stability.

As a person of skill in the art would understand, the present invention encompasses any reasonable combinations of the illustrated embodiments disclosed herein, which would provide a beneficial effect to a cancer patient.

The terminology used in the description of the invention herein is for describing particular embodiments only and is not intended to be limiting of the invention. As used herein, the singular forms "a," "an," and "the" are intended to include the plural forms as well, and vice versa, unless the context clearly indicates otherwise.

The term "about," as used herein, is intended to mean up to ±10% of an indicated value. Any ranges mentioned in the specification or the claims are to be understood as including the range itself and anything subsumed therein, including both endpoints.

The term "alkyl" refers to monovalent or divalent saturated alkane radical groups particularly having up to about 18 carbon atoms, more particularly as a lower alkyl, from 1 to 8 carbon atoms and still more particularly, from 1 to 6 carbon atoms. The hydrocarbon chain may be either straight-chained or branched. The term "C1-C10 alkyl" refers to alkyl groups having 1, 2, 3, 4, 5, 6, 7, 8, 9 or 10 carbon atoms. Similarly, the term "C1-C6 alkyl" refers to alkyl groups having 1, 2, 3, 4, 5, or 6 carbon atoms. Non-limiting examples include groups such as methyl, ethyl, n-propyl, isopropyl, n-butyl, iso-butyl, tert-butyl, n-hexyl, n-octyl, tert-octyl and the like.

The term "aryl" refers to a monovalent or divalent aromatic hydrocarbon group derived by the removal of one hydrogen atom from a single carbon atom of a parent aromatic ring system. Typical aryl groups include, but are not limited to, groups derived from aceanthrylene, acephenanthrylene, anthracene, azulene, benzene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenyl, phenanthrene, picene, and the like. Particularly, an aryl group comprises from 6 to 14 carbon atoms.

The term "amino" or "amine" when describing a group instead of a neutral molecules refers to a primary group (—$NH_2$), a secondary amino (e.g. monoalkyl-NH radical) or a tertiary amino group (dialkyl-N radical). In the context of an alkyl being interrupted by an amino group, the amino can also refer to a di-radical.

The term "biologically active moiety" refers to an organic structure that facilitates the absorption or delivery of a platinum-containing compound or enhances the therapeutic activity of the compound.

The term "carrier" refers to a chemical compound that facilitates the incorporation of a compound into cells or tissues.

The term "cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methyl-cyclopropyl, 2-methylcyclopentyl, 2-methylcyclooctyl, and the like, and multiple ring structures such as adamantanyl, and the like.

The term "halogen" refers to F, Cl, Br, or I.

The term "heterocyclic" refers to a monovalent or divalent ring derived by the removal of one or more ring atoms from the parent aryl or cycloalkyl. Typical aromatic heterocyclic or heteroaryl groups include, but are not limited to, groups derived from acridine, carbazole, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred.

The term "therapeutically effective amount" refers to an amount of a compound or a conjugate effective to prevent, alleviate or ameliorate symptoms of disease or prolong the survival of the subject being treated. Determination of a therapeutically effective amount is well within the capability of those skilled in the art, especially in light of the detailed disclosure provided herein.

The term "pharmaceutical composition" refers to a mixture of a compound or a conjugate disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "physiologically acceptable" or "pharmaceutically acceptable" refers to a carrier or diluent that does not abrogate the biological activity and properties of the compound.

The term "subject" refers to a mammalian animal or a human.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. "Prophylactic treatment" is to be construed as any mode of treatment that is used to prevent progression of the disease or is used for precautionary purpose for persons at risk of developing the condition.

The term "triazole" includes any structure that is formed from click chemistry. For example, the fused multi-ring structure formed from Dibenzocyclooctyne Group (DBCO) and an azide through Copper-free Click Chemistry is a triazole type structure.

An aspect of the invention provides a compound or payload or a pharmaceutically acceptable salt thereof. The compound/payload generally has the following formula: E-A-F. F is a functionalized platinum-acridine agent. E is a linker. A is a linkage group between E and F.

The functionalized platinum-acridine agent F can be further represented with the following general Formula I:

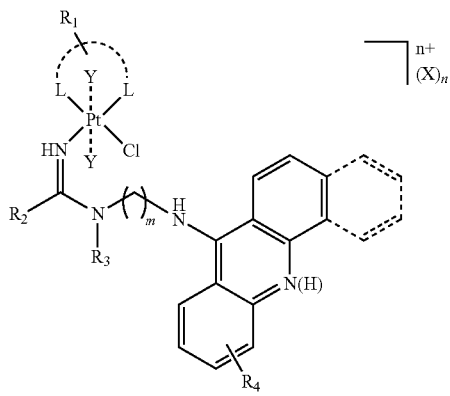

E, $R_1$, $R_2$, $R_3$, and $R_4$ each represent alkyl, alkenyl, alkynyl or any combination thereof. One or more of the carbon atoms in these groups can be replaced with a heteroatom (e.g. O, nitrogen, S). These groups can also contain one or more functionalities, which include for example, amide, azide, alkyne, hydrazide, ester, amide, carbamate, carbonate, ketone, oxo, carboxylate, disulfide, hydroxyl, amine, maleimide, N-hydroxysuccinimide, and other elements commonly used in ADC technology. Non-limiting examples include alkylene chains, (poly)ethyleneglycol chains, and oligopeptides. One or more of these functionalities are positioned at the terminal end of $R_1$, $R_2$, $R_3$, and/or $R_4$ for forming linkage A and connect with linker E. However, a functionality can also be located away from the terminal position, as long as it forms a desirable linkage with another linker or spacer. X is nitrate, halide (e.g. bromide, chloride), sulfate or $-OC(O)C_{1-10}$ alkyl. Each L represents an amine ligand where the nitrogen coordinates to the metal, and two Ls may link up as a diamine. Y is an additional axial ligand in octahedral Pt(IV) compounds and non-limiting examples include $Cl^-$, $OH^-$, $CH_3COO^-$, and $RCOO^-$ (R is an alkyl or aryl). n is 1, 2, 3 or 4. The length of the carbon chain in F may vary and m is 1, 2, 3, 4, 5 or 6. The dotted line represents an optional structural moiety. For example, the extended aromatic system can be a 3-ring acridine or a 4-ring benzacridine.

In some embodiments, the variables of Formula I are defined as follows:

$R_1$ represents an optional substituent of L and is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, (mono-, di-, or trihalogeno)methyl, or $C_{1-10}$ alkoxy;

$R_2$ and $R_3$ each independently represents (Radical) $C_{1-10}$ alkyl, wherein the $C_{1-10}$alkyl is optionally (a) interpreted with one or more structural moieties selected from the group consisting of amino, oxygen, sulfur, amide, ester, carbamate, sulfonamide, sulfonyl, carbonate, ketone, disulfide, $(CH_2CH_2O)_p$ wherein p is an integer of 1 to 10, aryl or 5 to 12 membered aromatic or non-aromatic heterocyclic group; or (b) substituted with one or more structural moieties selected from the group consisting of hydroxy, imino, oxo, cyano, $C_{1-10}$alkoxy, $C_{1-10}$ alkylthio, $C_{1-6}$ alkylsulfonyl, di-$C_{1-10}$ alkylamine, aryl or 5 to 12 membered aromatic or non-aromatic heterocyclic group;

$R_4$ is selected from the group consisting of halogen, cyano, nitro, $C_{1-10}$ alkylthio, $C_{2-10}$ alkenyl, $C_{2-10}$ alkynyl, $C_{1-10}$ alkoxy, amino (e.g. $-NH_2$, $C_{1-10}$ monoalkylamino, $C_{1-10}$ dialkylamino, $C_{1-10}$ alkyl, $-NHC(O)$ $C_{1-10}$ alkyl, $-C(O)NHC_{1-10}$ alkyl, or (mono-, di-, or trihalogeno)methyl; the acridine or benzacridine moiety can be substituted with one or more $R_4$;

each L represents $NH_3$ or an amine ligand wherein the nitrogen of $NH_3$ or the amine ligand coordinates to Pt(IV), further wherein the two amine ligands optionally link up to form a diamine/chelate; Non-limiting examples of amine ligand includes $C_{1-10}$ alkyl $NH_2$ wherein the alkyl can be optionally substituted with one or more $R_4$.

Non-limiting examples of ligands having a coordinating nitrogen include the following:

a

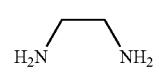

-continued

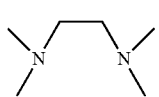
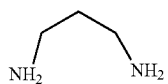
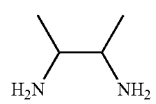
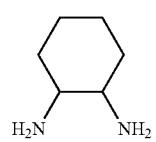
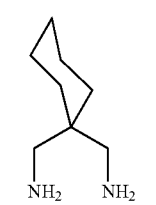
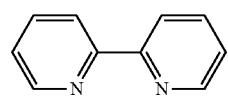
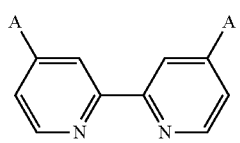
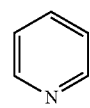

NH$_3$

NH$_2$R$_{13}$

NH(R$_{13}$)$_2$

N(R$_{13}$)$_2$

Wherein R$_{13}$ is independently C$_1$-C$_6$alkyl.

In some embodiments, the two L ligands link up to form NH$_2$—(CH$_2$)$_v$—NH$_2$, wherein v is 1, 2, 3, 4 or 5.

In some embodiments, the diamine ligands include the following:

  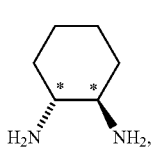

-continued

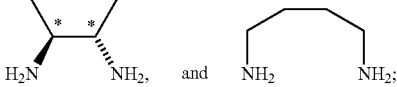

X is nitrate or halide;

Y is an optional ligand, wherein when Y is present, Pt is Pt(IV), and when Y is void, Pt is Pt(II);

A is a linkage comprising one or more structural moieties selected from the group consisting of ester, amide, amino, carbamate, hydrazide, triazole, and disulfide, and A links E to a terminal end of one of R$_2$ and R$_3$;

E is a linker comprising a free terminal functional group capable of forming an amide or a thio-ether upon contact with an amino group or a thiol, respectively. Alternatively, E can contain an strained alkyne or an azide for click chemistry to form a triazole moiety.

m is 1, 2, 3, 4, 5 or 5; and n is 1, 2, 3 or 4.

In some embodiments, n is 1 or 2. In some embodiments, m is 1 or 2.

In some embodiments, E further comprises C$_{1-10}$alkyl, wherein the C$_{1-10}$alkyl is optionally (a) interpreted with one or more structural moieties selected from the group consisting of amino, oxygen, sulfur, amide, ester, carbamate, sulfonamide, sulfonyl, carbonate, ketone, disulfide, (CH$_2$CH$_2$O)$_p$ wherein p is an integer of 1 to 10, aryl or 5 to 12 membered aromatic or non-aromatic heterocyclic group; or (b) substituted with one or more structural moieties selected from the group consisting of hydroxy, imino, oxo, cyano, C$_{1-10}$ alkoxy, C$_{1-10}$ alkylthio, C$_{1-6}$ alkylsulfonyl, di-C$_{1-10}$ alkylamine, aryl or 5 to 12 membered aromatic or non-aromatic heterocyclic group.

In non-limiting examples, E, R$_2$ and R$_3$ independently include the following:

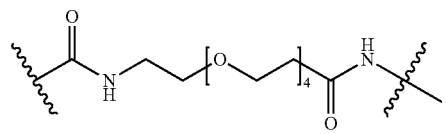

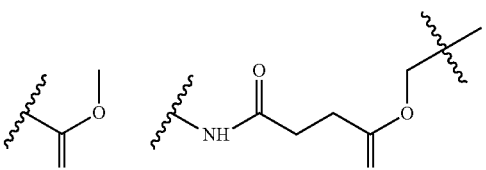

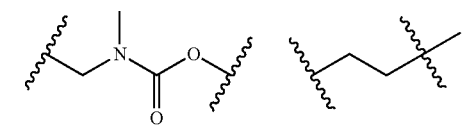

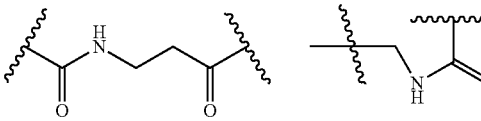

-continued

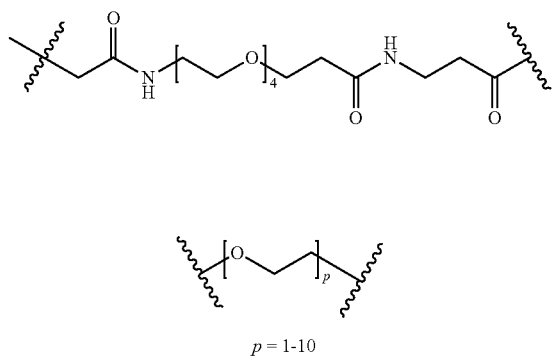

$p = 1-10$

In some embodiments, the free terminal functional group is capable of forming a new amide or a thioether linkage when reacting with a nucleophile. Non-limiting examples of the terminal functional groups include:

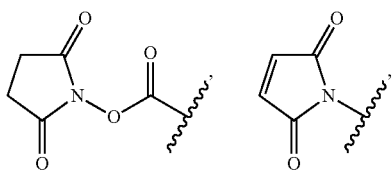 [SMILES: *C(=O)ON1C(=O)CCC1=O ; *N1C(=O)C=CC1=O]

a haloacetamide (e.g. Cl-acetamide, Br-acetamide, I-acetamide), a strained alkyne, an azido group (—N$_3$) and a hydrazine group. These functional groups are capable of reacting with a counterpart functional group (e.g. a nucleophilic group, an azido, a strained alkyne) on unnatural or engineered residues of a precursor of a biologically active moiety to form a conjugate.

In some embodiments, Formula I is represented as I', where two amine ligand L link up as a diamine ligand. In some embodiments, the two L ligands linked up to form 1,2-diaminoethane, or 1,3-diaminopropane. An exemplary formula having a diamine ligand is as follows:

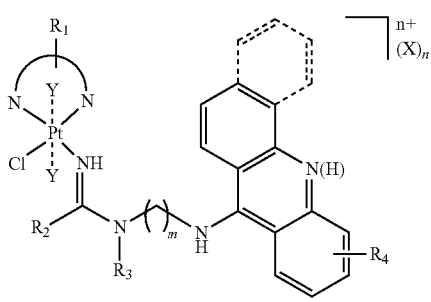

In some embodiments, Y is present, and Pt is Pt(IV). In some embodiments, Y is Cl, Pt is Pt(IV), and the two L ligands link together to form 1,3-diaminopropane.

It should be noted that Formula IIb having Pt(IV) can be readily prepared from Formula IIa by reaction with iodobenzene dichloride.

Pt(II) and Pt(IV) Compounds

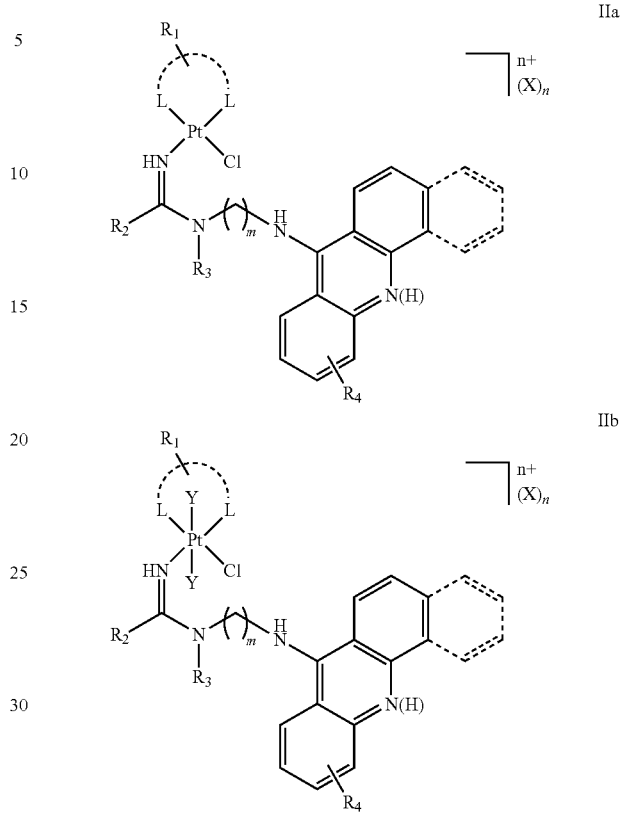

The substituents of Formula IIa and IIb are defined as follows:

R$_1$ represents a substituent of L and is selected from the group consisting of hydrogen, halogen, cyano, nitro, mercapto, C$_{1-10}$ alkylthio, C$_{2-10}$ alkenyl, C$_{2-10}$ alkynyl, C$_{1-10}$ alkoxy, C$_{1-10}$ dialkylamino, C$_{1-10}$ alkyl, (mono-, di-, or trihalogeno)methyl, or C$_{1-10}$ alkoxy;

R$_2$ and R$_3$ each independently represents C$_{1-10}$ alkyl, wherein the C$_{1-10}$ alkyl is optionally
a) interpreted with one or more structural moieties selected from the group consisting of amino, oxygen, sulfur, amide, ester, carbamate, sulfonamide, sulfonyl, carbonate, ketone, disulfide, (CH$_2$CH$_2$O)$_p$ wherein p is an integer of 1 to 10, aryl or 5 to 12 membered aromatic or non-aromatic heterocyclic group; or
(b) substituted with one or more structural moieties selected from the group consisting of hydroxy, imino, oxo, cyano, C$_{1-10}$ alkoxy, C$_{1-10}$ alkylthio, C$_{1-6}$ alkylsulfonyl, di-C$_{1-10}$ alkylamine, aryl or 5 to 12 membered aromatic or non-aromatic heterocyclic group;

R$_4$ is selected from the group consisting of halogen, cyano, nitro, C$_{1-10}$ alkylthio, C$_{2-10}$ alkenyl, C$_{2-10}$ alkynyl, C$_{1-10}$ alkoxy, C$_{1-10}$ dialkylamino, C$_{1-10}$ alkyl, or (mono-, di-, or trihalogeno)methyl. The acridine or benz-acridine moiety can be substituted with one or more R$_4$. In some embodiments, R$_4$ is independently an amino, a nitro, —NHC(O) C$_{1-10}$ alkyl, —C(O)NH C$_{1-10}$ alkyl, or halo;

X is nitrate or halide;

Y is chloride, and Pt is Pt(IV);

m is 1, 2, 3, 4, 5 or 5; and n is 1, 2, 3 or 4; and each L represents NH$_3$ or an amine ligand wherein the nitrogen coordinates to Pt, further wherein the two amine ligands optionally link up to form a diamine/chelate.

Conversion of Pt(II) to Pt(IV) can take place at different stages of the synthesis of the warhead. As illustrated below, a Pt(II) compound (e.g. platinum-acridines) is converted to a Pt(IV) compound via iodobenzene dichloride. Alternatively, the conversion can occur prior to the incorporation of the aromatic moiety.

Conversion of platinum (II)-acridine to Pt(IV)-acridine

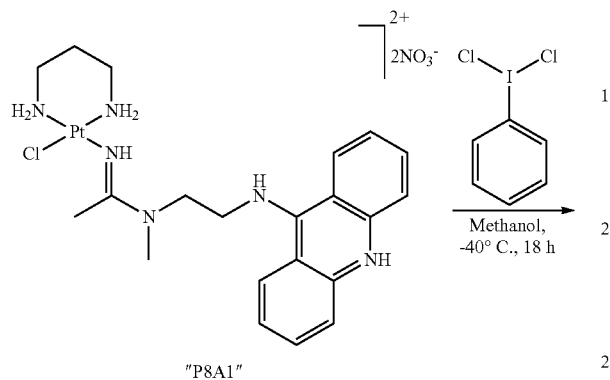

"P8A1"

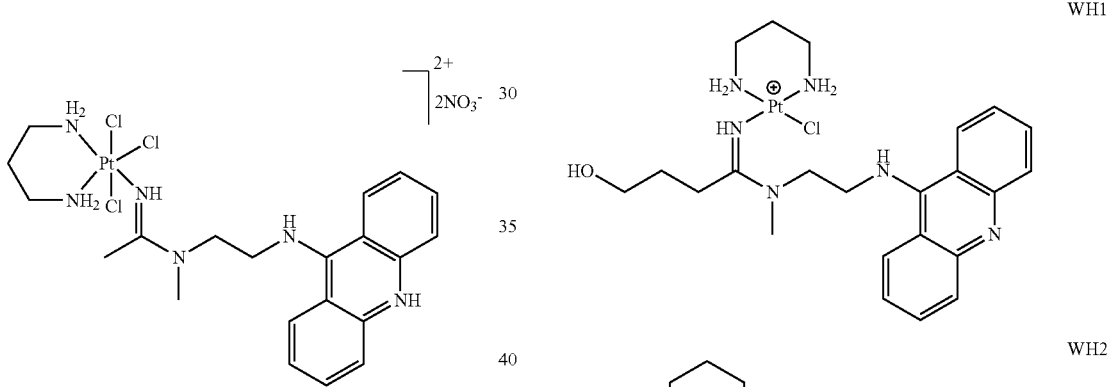

Conversion of platinum (II) to Pt(IV) prior to the incorporation of acridine moiety

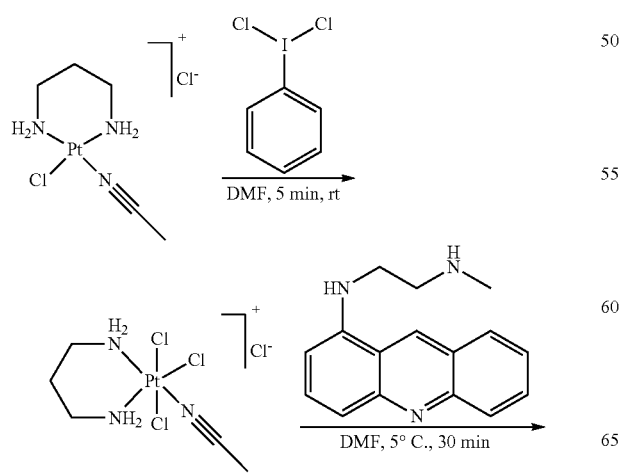

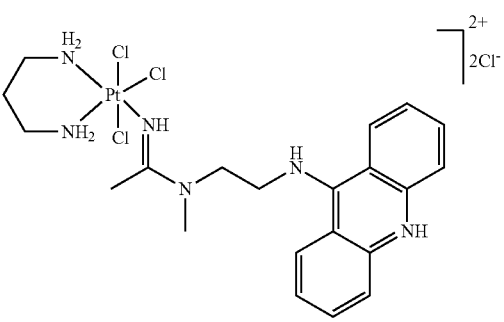

Various Pt warheads can be incorporated into F, a component of the compound of Formula I. Non-limiting examples of the functionalized platinum-acridines as warheads include:

Examples of ketone/oxo-modified warheads

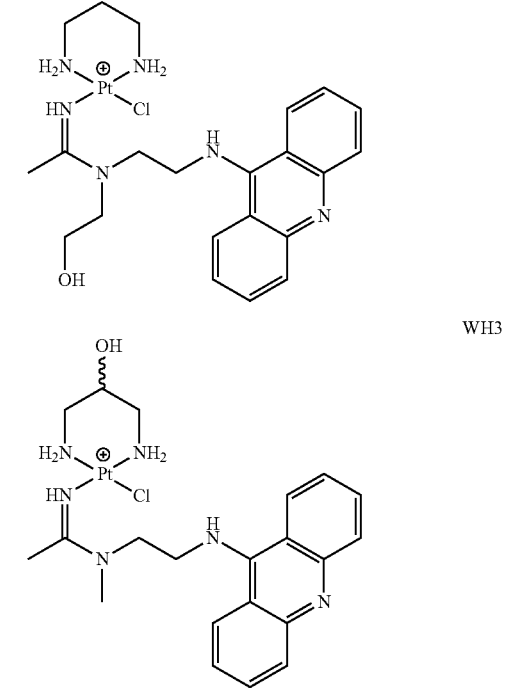

WH1

WH2

WH3

-continued
Examples of carboxylic acid-modified wardheads

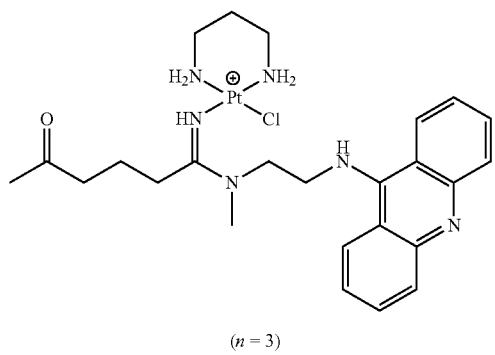
WH4
(n = 3)

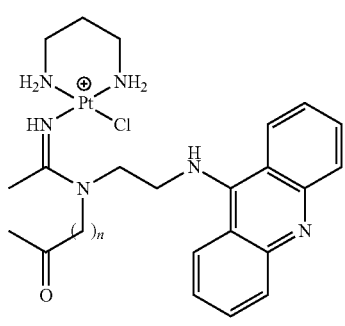
WH5
n = 1, 2, 3, 4, 5 or 6

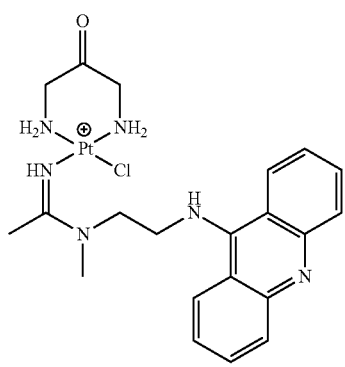
WH6

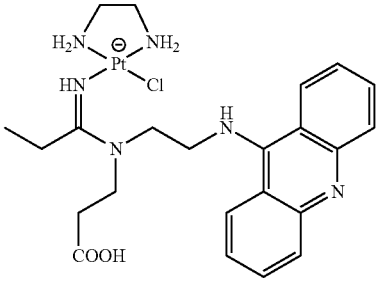
WH7

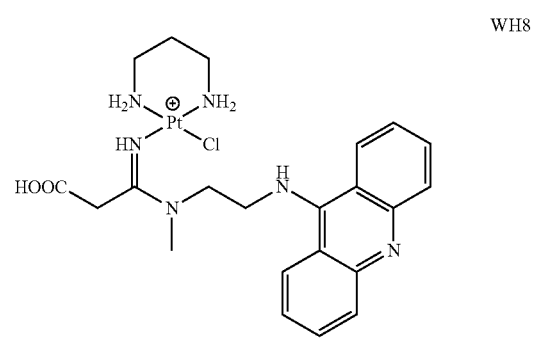
WH8

One or more of the functionalities of E, $R_1$, $R_2$, $R_3$, and/or $R_4$ can be linked up to form a linker extension module. These modules serve to extend the linker of E or F, connect E with F, or conjugate the payload with the carrier. For example, DBCO-MAL and DBCO-PEG4-MAL can use used to connect E with F through the formation of a triazole ring utilizing copper free click chemistry. Meanwhile, the maleimide (MAL) moiety can be conjugated to an mAb. Succinic anhydride can react with an amino group or a hydroxyl group to form succinic-amid or succinic-ester to extend the linker and provides a carboxylic acid to further functionalize and conjugate the payload. The modules of azido-PEG-acid, azido-hydrazide, and azido-amine similarly extend a linker and set up an azido group for click chemistry.

Examples of Linker Extension Module

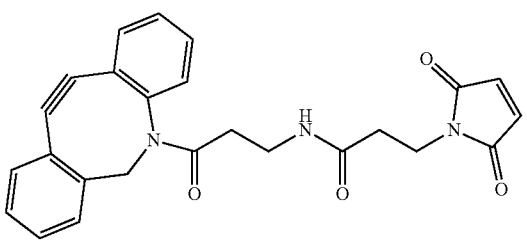
DBCO-MAL

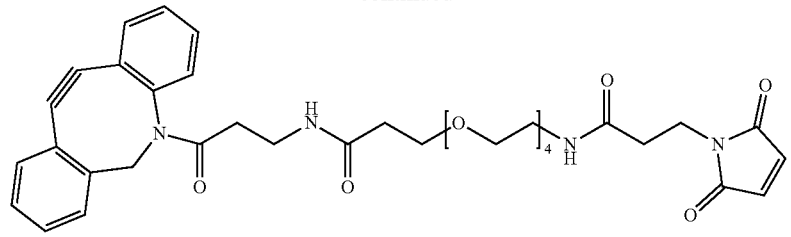

DBCO-PEG4-MAL

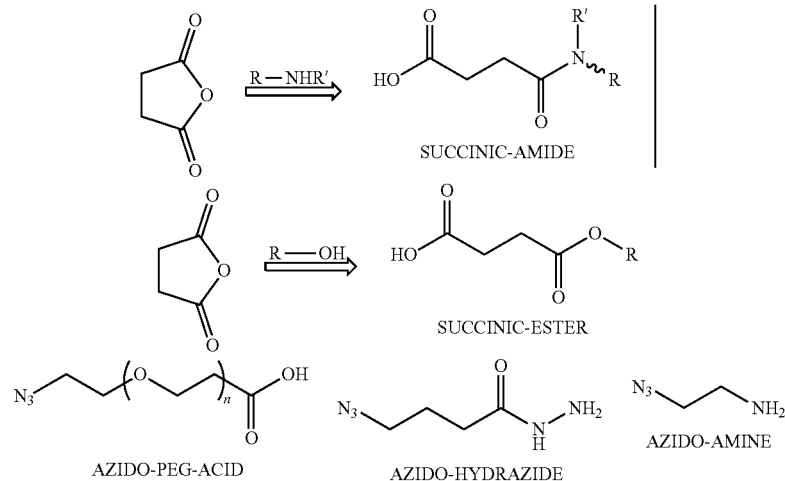

The linkage A between E and F can be any suitable groups including for example, ester, amide, carbamate, hydrazide, and triazole. In some embodiments, A contains a cleavable group via enzymatic dipeptide cleavage, pH-sensitive cleavage, platinum-mediated hydrolytic ester cleavage, or self-immolative linker degradation. In non-limiting examples, A contains one or more of the following moieties:

-continued

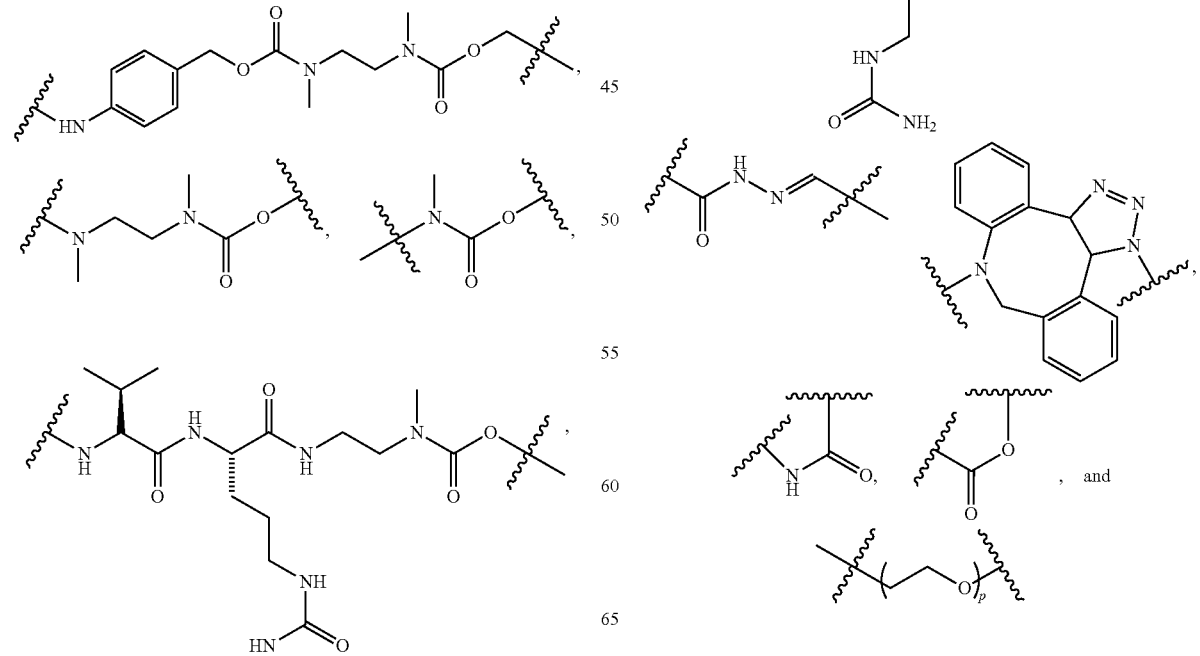

wherein p is 1-10

Of course, any of the above moieties can also be included in E, $R_2$ and/or $R_3$. In some embodiments, the linkage is a triazole formed from the reaction between a strained alkyne and an azido group.

In some embodiments, one of the E and F precursors thus contains the azido group and the other of the pair contains the strained alkyne. In some embodiments, a precursor of E contains the strained alkyne and a precursor of F contains the azido group.

In illustrative embodiments, payloads PL1 and PL2 are synthesized by extending WH7 with AZIDO-AMINE and subsequent click chemistry with cyclooctyne-maleimide linker modules (DBCO-MAL and DBCO-PEG4-MAL) to generate cysteine-reactive payloads. E is derived from an extension module having a strained alkyne. F is derived from a functionalized warhead having an azido group, which reacts with the strained alkyne to form triazole linkage A.

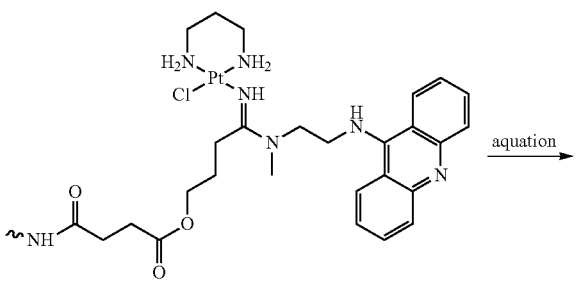

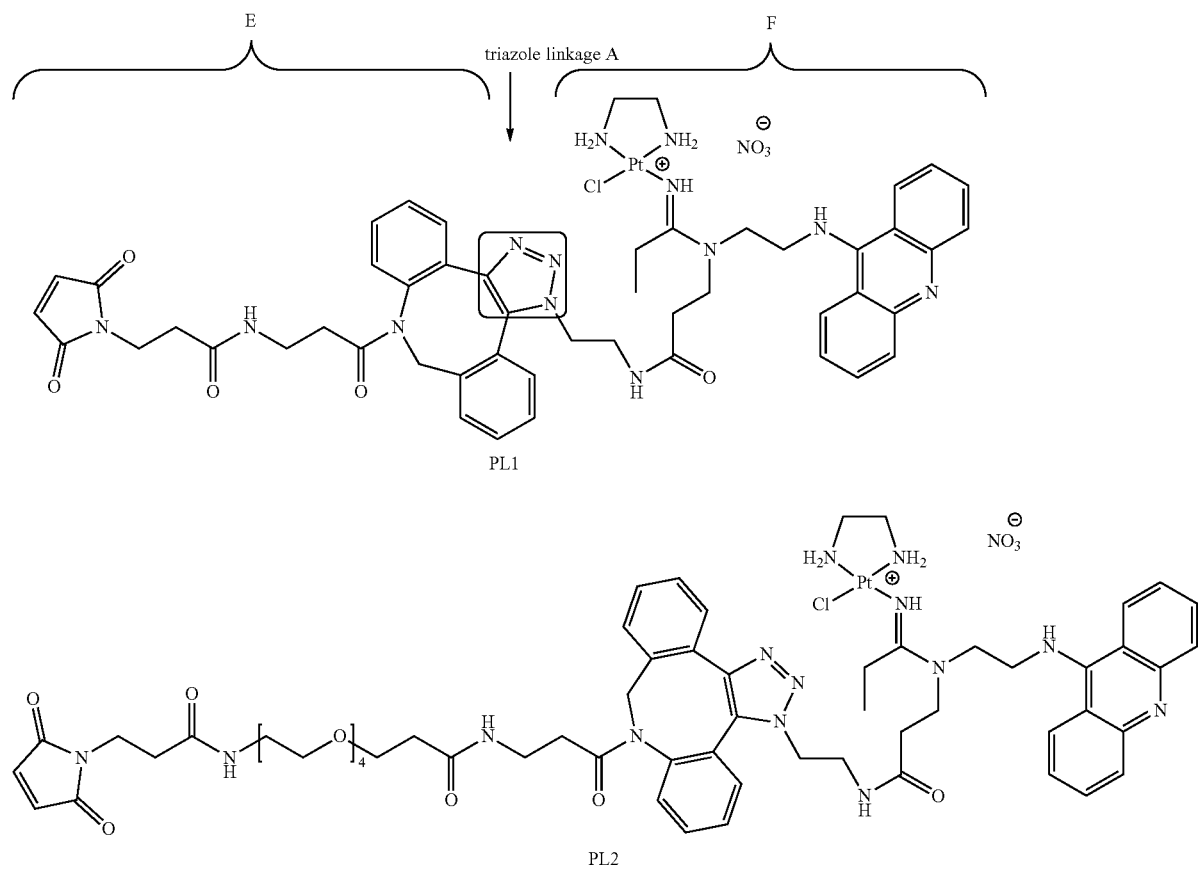

These functionalized platinum-acridines as warheads can be released from the payload via various mechanisms. Non-limiting examples of release mechanisms include enzymatic dipeptide cleavage, pH-sensitive cleavage, platinum-mediated hydrolytic ester cleavage, and self-immolative linker degradation.

In illustrative embodiments, the warhead is released via a reaction triggered by Pt-promoted intracellular ester cleavage in low-chloride cytosolic environment.

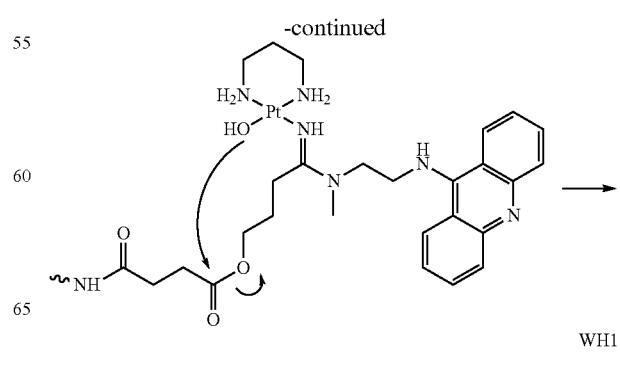

In further illustrative embodiments involving enzymatically cleavable, self-immolative valine-citrulline-carbamate linkers, two payloads (PL5, PL6) are synthesized based on a cathepsin B cleavable dipeptide sequence (lysosomal degradation). These molecules are designed to release OH-modified warheads, such as WH1-3. Other dipeptide target sequences of relevant proteases can be incorporated as well.

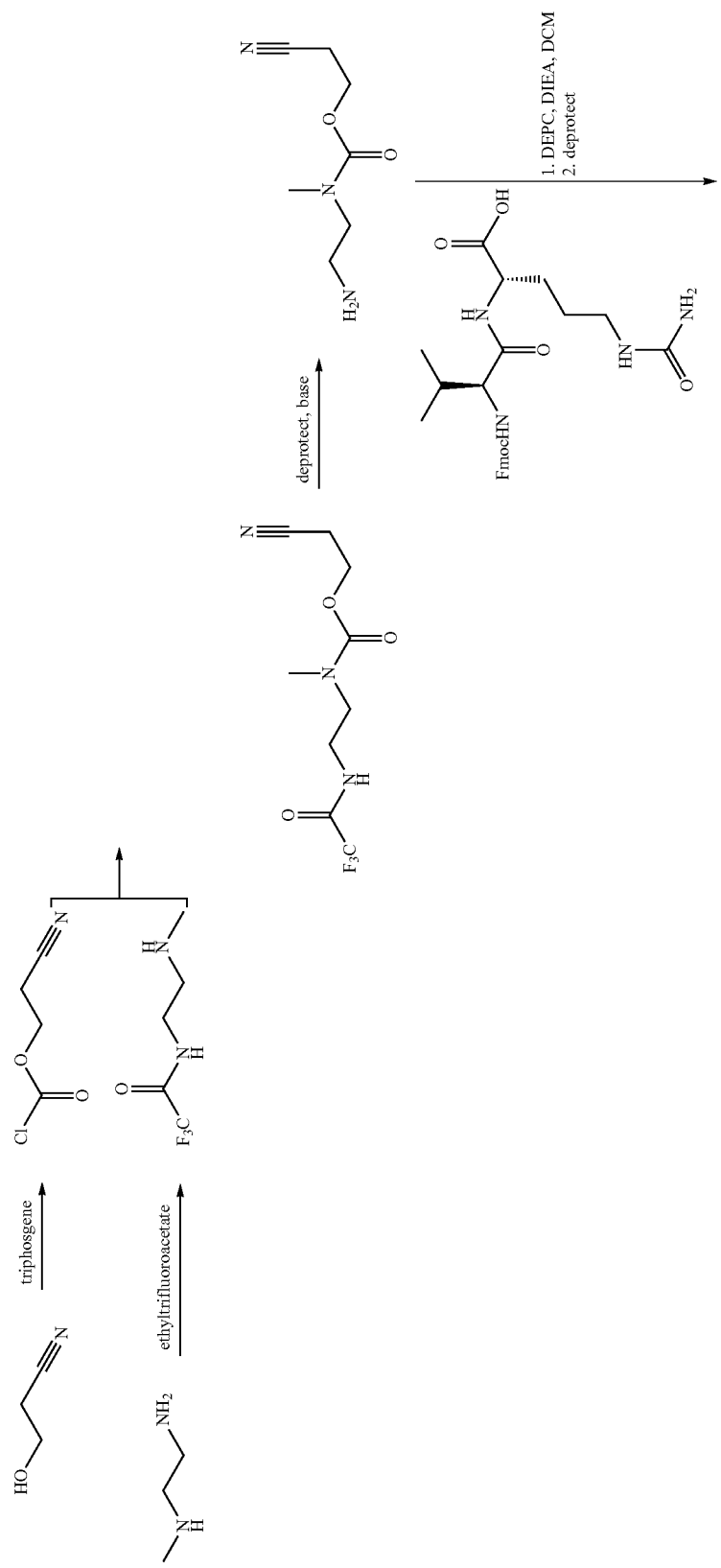

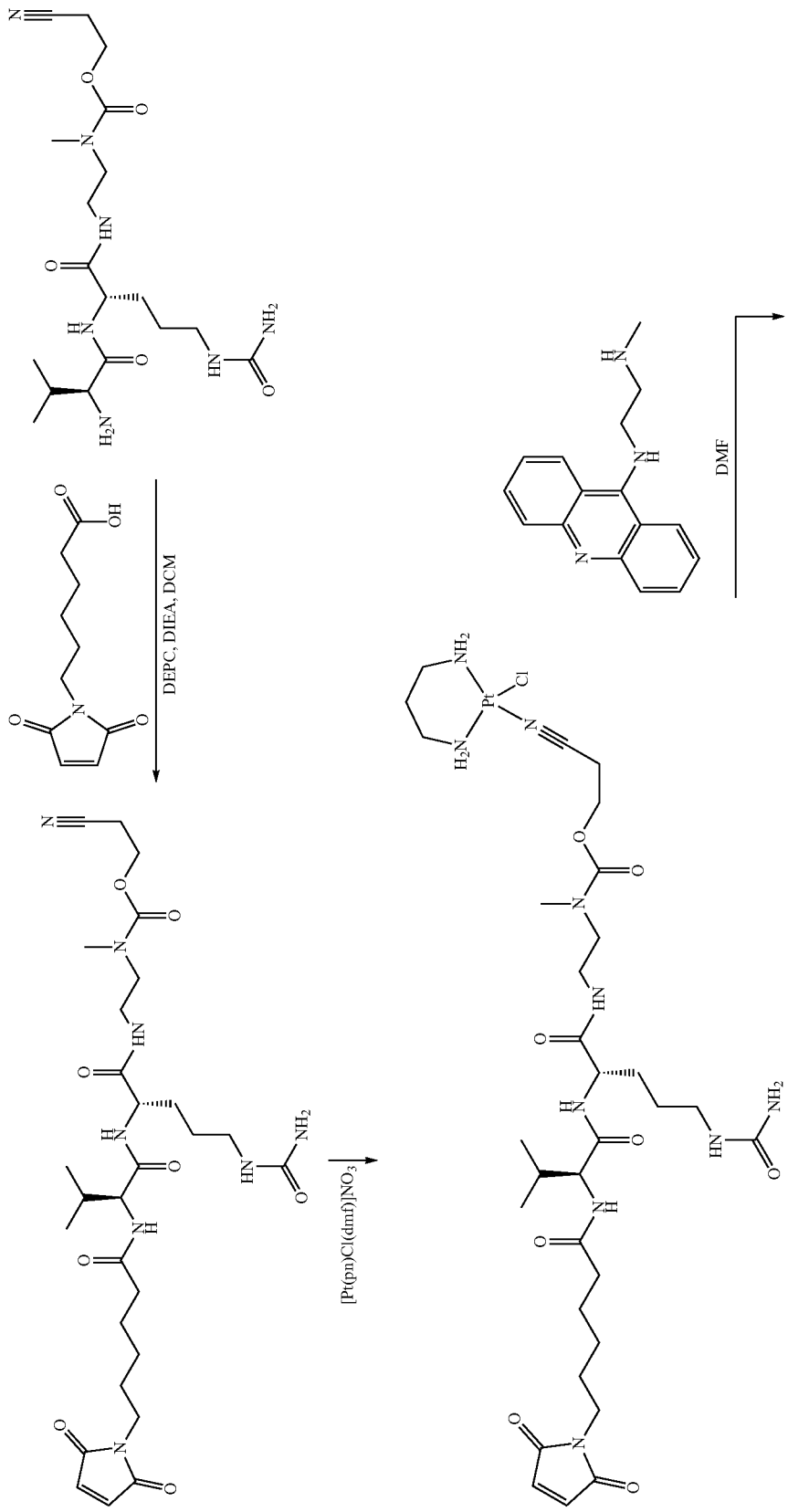

-continued
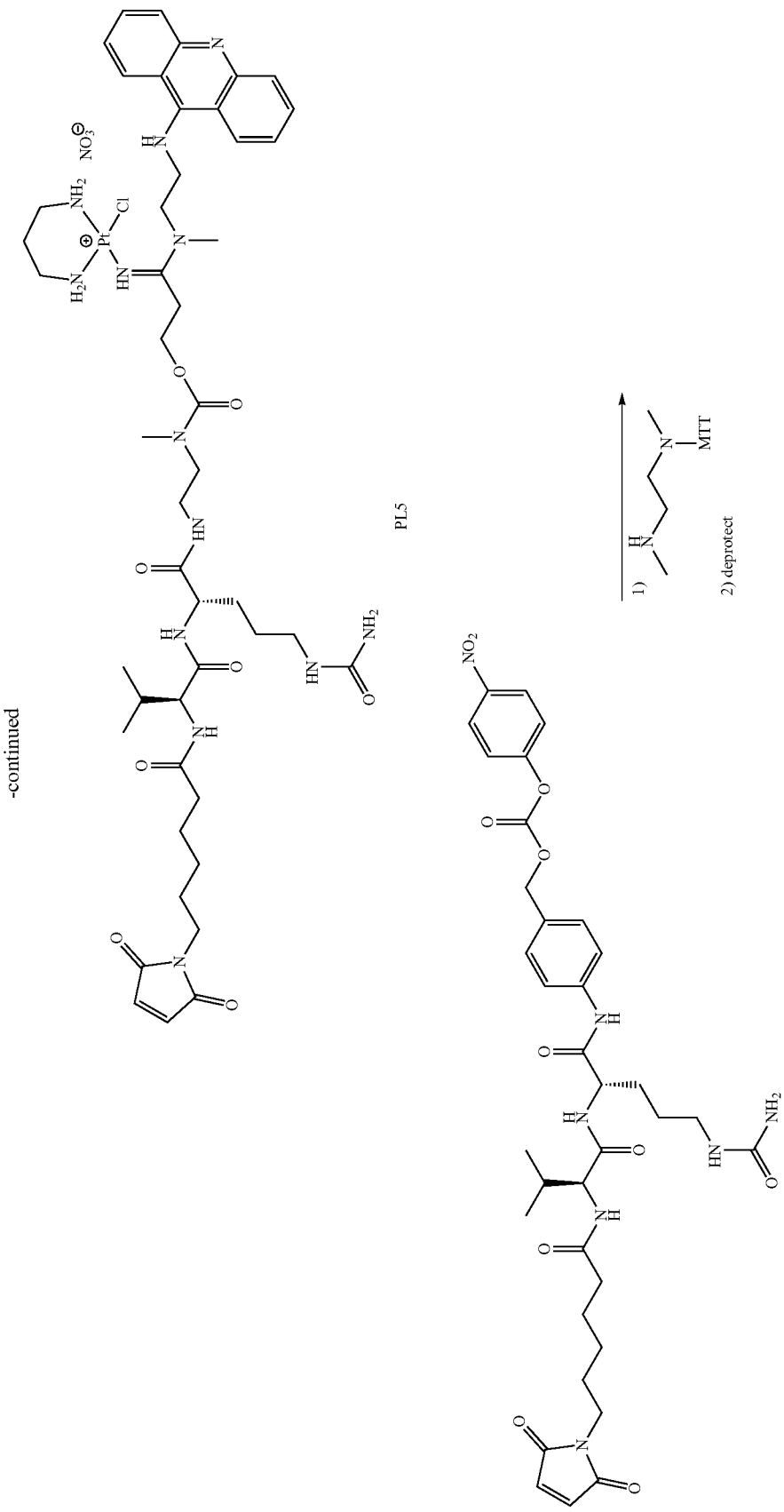
PL5

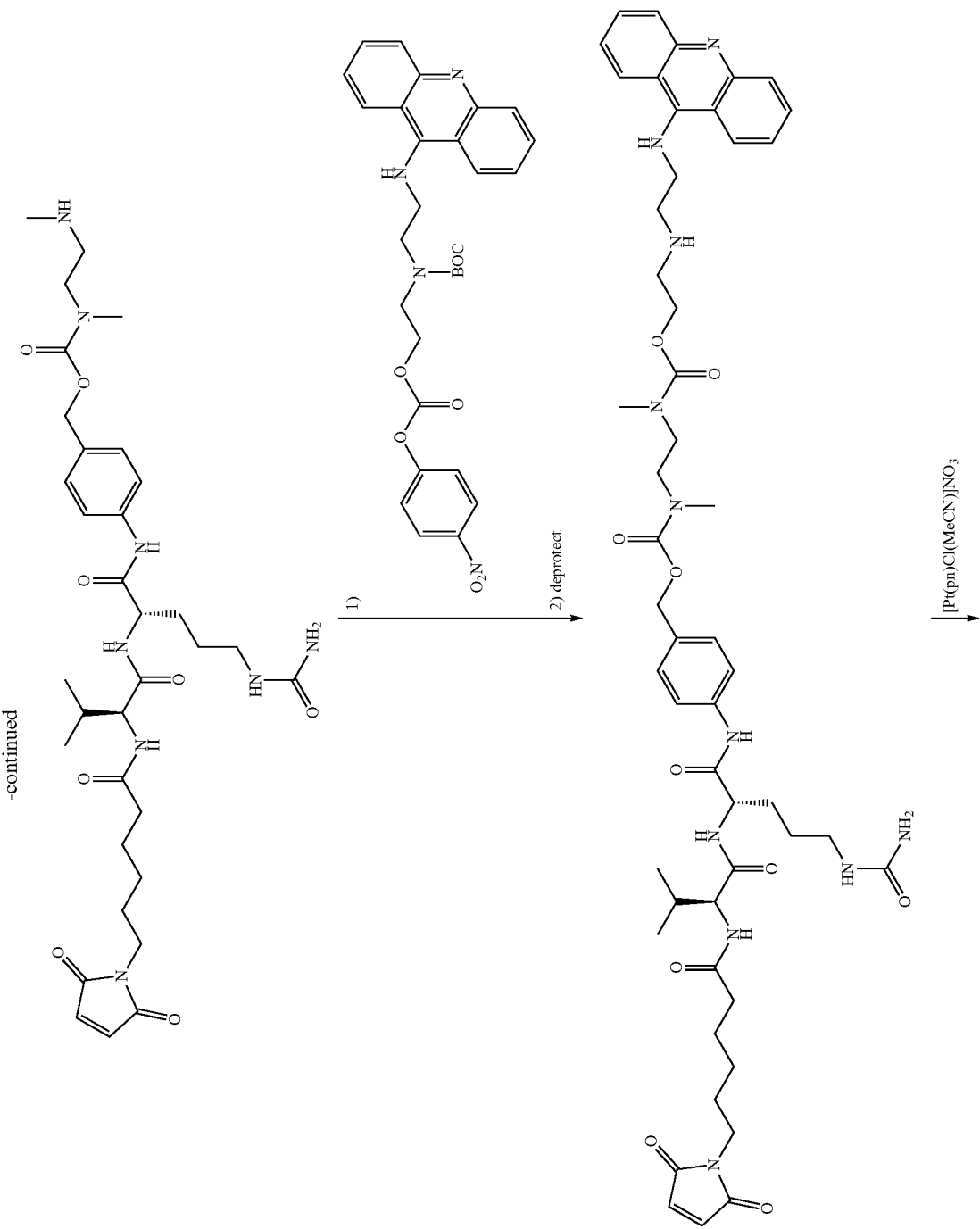

-continued
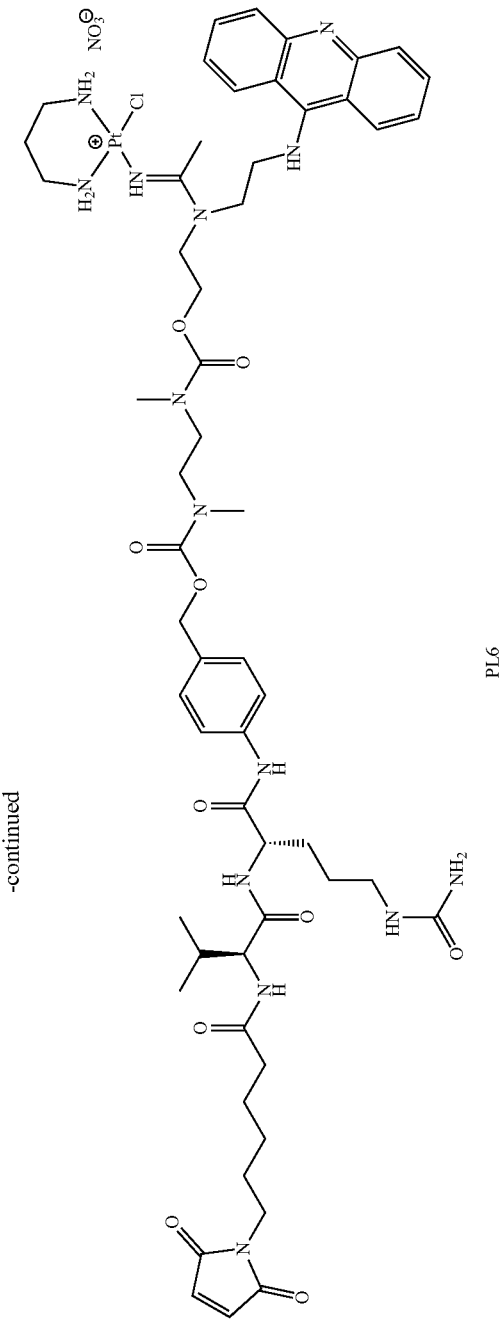
PL6
alternative extension to mAb binding group:
1. use of Fmoc-protected N-terminal Valine
2. diprotection
3. coupling of AZIDO-PEG-ACID
4. copper-free click chemistry to extend linker with DBCO-MAL
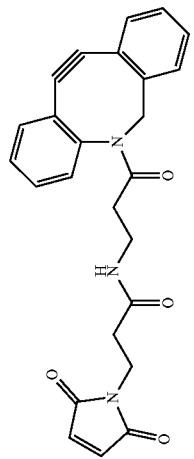

Warheads are subsequently released from the payload via enzymatic cleavage, self-immolation, and lysosomal escape. Certainly, more than one cleavage and release mechanism can be incorporated into a single payload depending on the specific construct of the molecule and the target of interest.

The concept and synthesis disclosed in this patent document can be applied to other mono- and poly-cationic metallopharmaceuticals. Non-limiting examples include complexes of Pt(II)/Pt(IV), Au(I)/Au(III), Ru(II)/Ru(III), Cu(I)/Cu(II), Pd(II)/Pd(IV).

PL5

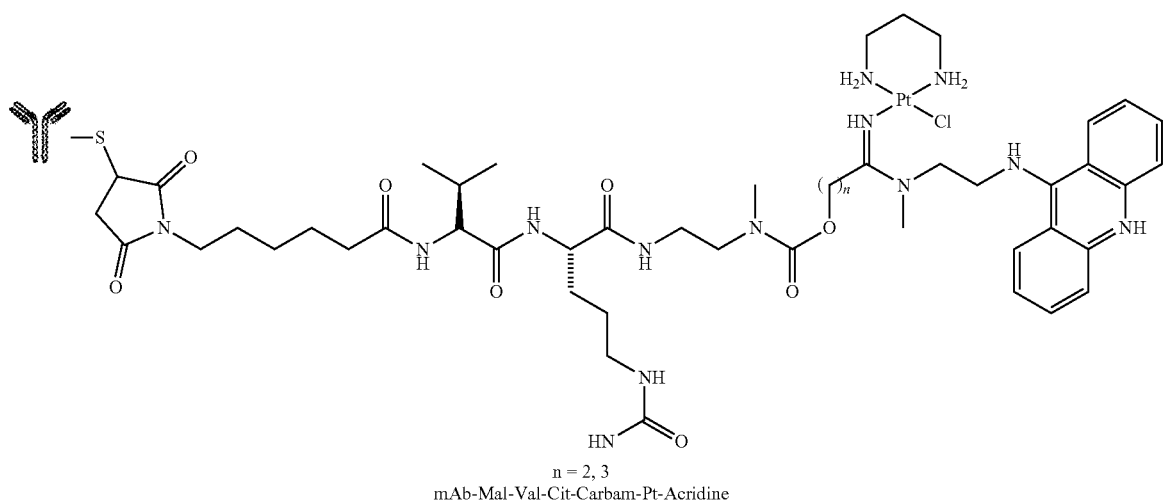

n = 2, 3
mAb-Mal-Val-Cit-Carbam-Pt-Acridine

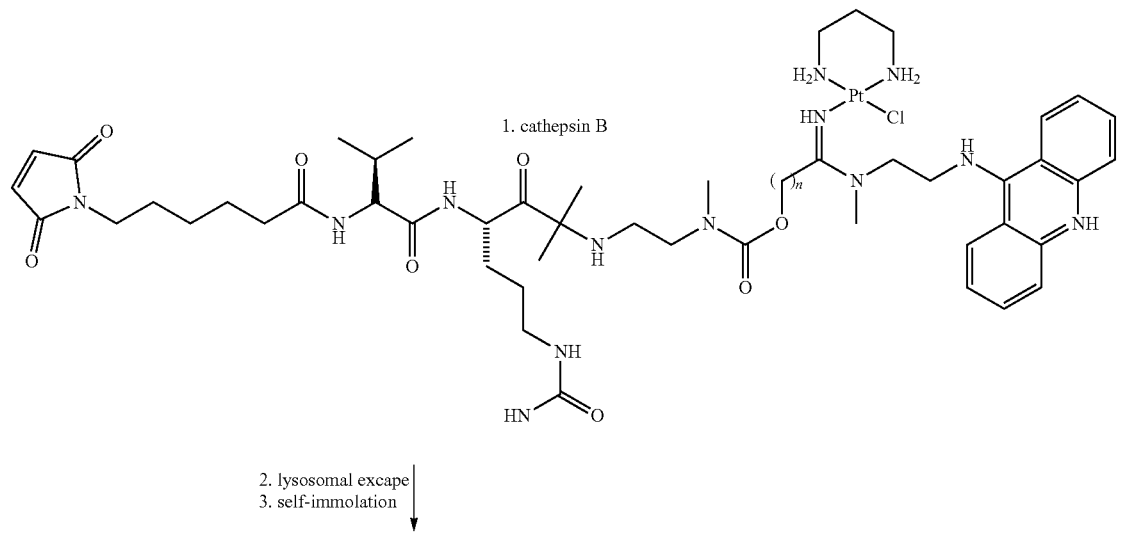

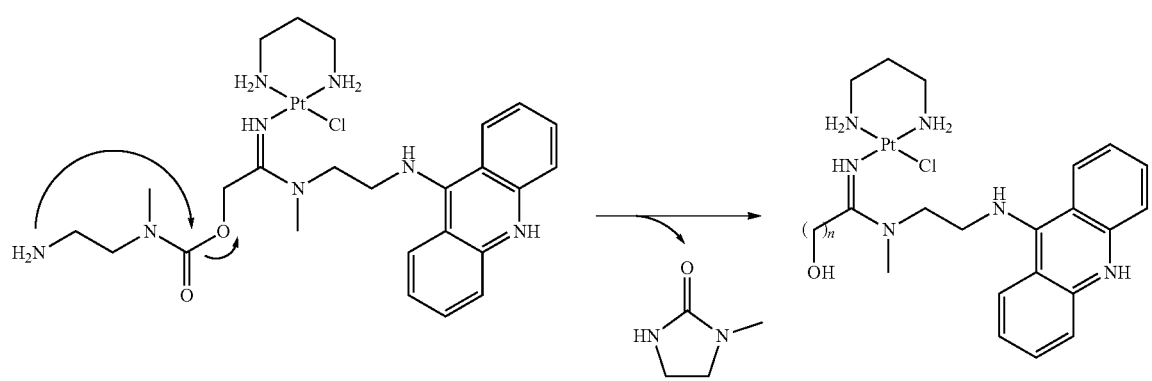

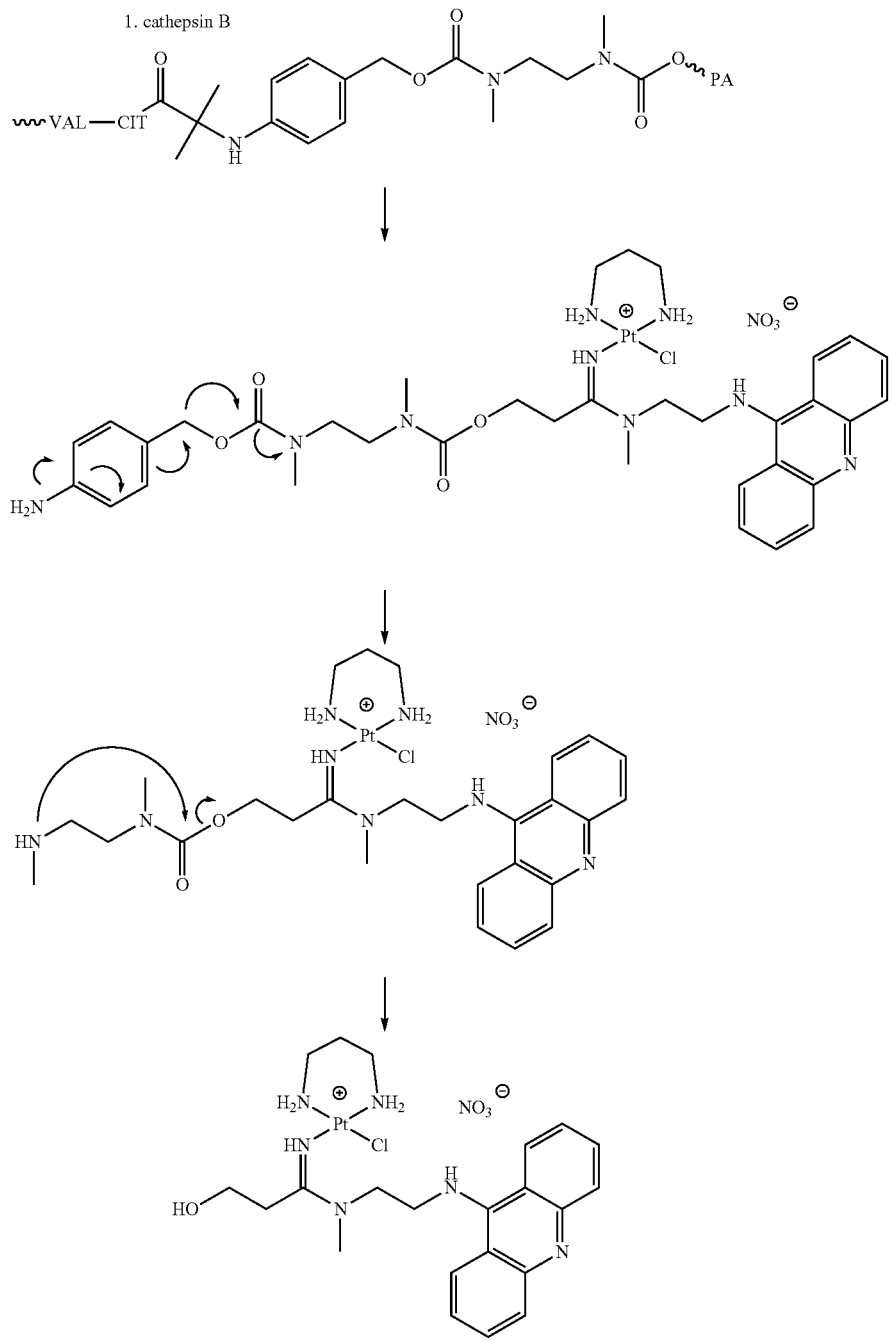

PL6

Another aspect of the invention provides a conjugate or a pharmaceutically acceptable salt of thereof, wherein the conjugate includes a biologically active moiety and the compound or payload described herein. The biologically active moiety is selected from the group consisting of a small molecule, a receptor-targeted vector, a nanoparticle and a polymer.

In some embodiments, the biologically active moiety is a receptor-targeted vector selected from the group consisting of aptamer, integrin-binding RGD peptide, serum protein, human serum albumin, transferrin, engineered mAbs, or any other cancer-specific biomolecule. In some embodiments, the biologically active moiety is a nanoparticle or a polymer selected from the group consisting of poly(N-(2-hydroxypropyl)methacrylamide (pHPMA), polyphosphazene, dendrimeric polymer, carbon nanotube, and mesoporous silica nanoparticles (MSN). In some embodiments, the biologically active moiety is a small molecule including for example, carbohydrates such as glucose, mannose, hyaluronic acid, chitosan; peptides such as poly(L-lysine), poly(L-arginine); folic acid; kinase inhibitors such as erlotinib, gefitinib (EGFR, Her2), ibrutinib (Bruton's kinase), imatinib (BCR-Abl); (growth) hormone-receptor antagonists (endoxifen, tamoxifen); micelle- and liposome-forming lipids such as 1,2-dipalmitoyl-sn-glycero-3-phosphorylglycerol sodium salt (DPPG), hydrogenated soybean phosphatidylcholine (HSPC), 1,2-distearoyl-sn-glycero-3-phosphoethanolamine (DSPE), proapoptotic agents and other chemo sensitizing agents, such as ursolic acid, oleanolic acid, curcumin, and suramin. In some embodiments, the biologically active moiety of the conjugate is an unnatural and/or site-specifically engineered protein residues.

Various peptides, polymers and nanoparticles can be conjugated to payloads for the delivery of warheads. For example, delivery vectors in which cell binding moieties (targeting ligand) other than monoclonal antibodies (mAbs) include aptamers, carbohydrates, peptides, integrin-binding RGD peptides, synthetic polymers. Further, the payload can also be conjugated to serum proteins, human serum albumin, transferrin or engineered mAbs.

In some embodiments, the conjugate includes a thioether, an amide, a carbamate, an ester and a disulfide as a linkage between the biologically active moiety and the payload. In some embodiments, the linkage is derived from the reaction between a nucleophilic group of a precursor of the biologically active moiety and a terminal functional group of E of the compound/payload. In some embodiments, the terminal function group is a maleimide or a N—O-succinimide ester (NHS ester). In some embodiments, the precursor of the biological active moiety contains a nucleophilic group such as the thiol group of cysteine or the amino group of lysine.

Another aspect of the invention provides a pharmaceutical composition containing the payload/compound or conjugate described herein or a pharmaceutically acceptable salt thereof, and a pharmaceutically acceptable carrier.

The pharmaceutical composition may also contain one or more physiologically acceptable carriers, diluents, excipients, smoothing agents, suspension agents, film forming substances, and coating assistants, or a combination thereof. Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

Another aspect of the invention provides a method of improving the efficacy or cytotoxicity of the Pt warhead and/or bioavailability of the warhead of the compound described herein. The method generally includes connecting a payload and a biologically active moiety through a linker. By conjugating the compound selectively to a biologically active moiety such as a carrier, the stability of the compound is improved. Meanwhile, the Pt warhead can be transported to the targeted disease area more efficiently. As a result, the cytotoxicity of the Pt warhead is enhanced. In some embodiments, the conjugate is formed after administering the payload to a subject. In some embodiments, the conjugate is prepared synthetically prior to being administered to a subject.

In some embodiments, the receptor-targeted vector is selected from a group consisting of aptamer, integrin-binding RGD peptide, serum protein, human serum albumin, transferrin, engineered mAbs, or any other cancer-specific biomolecule.

Like other potent small-molecule cytotoxins, platinum-acridines kill cancer cells at low-nanomolar concentrations but show unfavorable pharmacokinetic properties and dose-limiting systemic toxicity. By delivering them selectively to tumor tissue in the form of a conjugate, their drug-like properties are significantly improved.

In some embodiments, the receptor-targeted vector is a protein carrier. As is illustrated in the example section below, a protein carrier can conjugate selectively with the terminal functional group of the payload moiety without interference from potential chloride substitution of the platinum moiety. The resulting conjugates of platinum-acridines and protein carriers can be used to not only deliver these cytotoxics selectively to tumor tissue, but also facilitate their uptake into cancer cells lacking appropriate membrane-bound cation transporters by receptor-mediated and receptor-independent endocytosis. This modality applies to various proteins including for example serum proteins and antigen-targeted IgG-type antibodies.

The conjugate of the present invention can also be prepared in various approaches prior to being administered to a subject. The chemical connection (e.g. click chemistry and coupling reactions) between different moieties of the payload can also be applied to the conjugation between the biologically active moiety and the payload or an intermediary linker component. There is no limitation on the sequence of synthetic steps when preparing the conjugate. As illustrated below, the payload can be conjugated directly to a biologically active moiety through the terminal functional group (e.g. NHS ester in method 1). Alternatively, a protein can be first linked to an intermediate carrier through an intermediary linker having a terminal functional group for reacting with the protein. After the initial reaction, the other end of the intermediary linker connects to the payload moiety (e.g. click chemistry in method 2). In some embodiments, the protein or derivative thereof contains a nucleophilic group such as the thiol group of cysteine or the amino group of lysine.

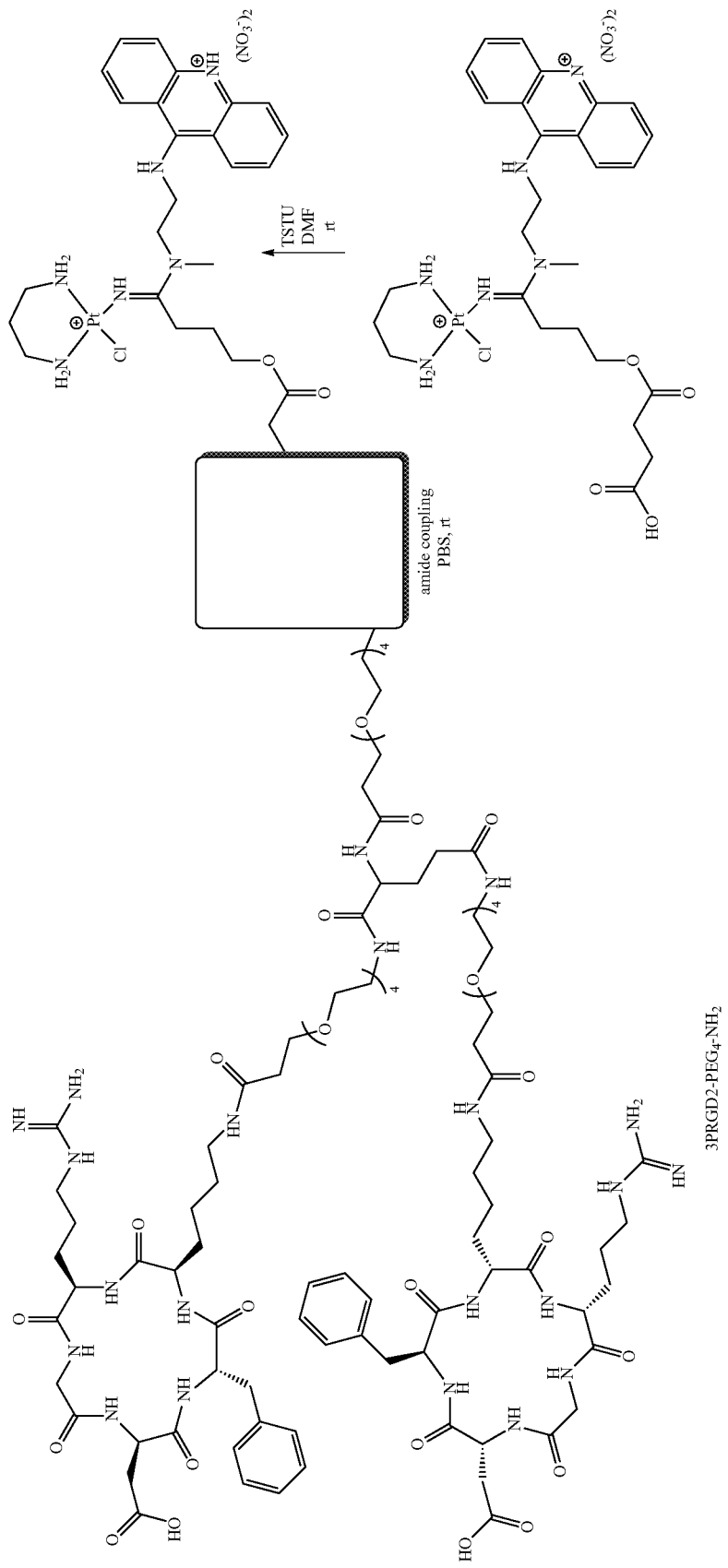

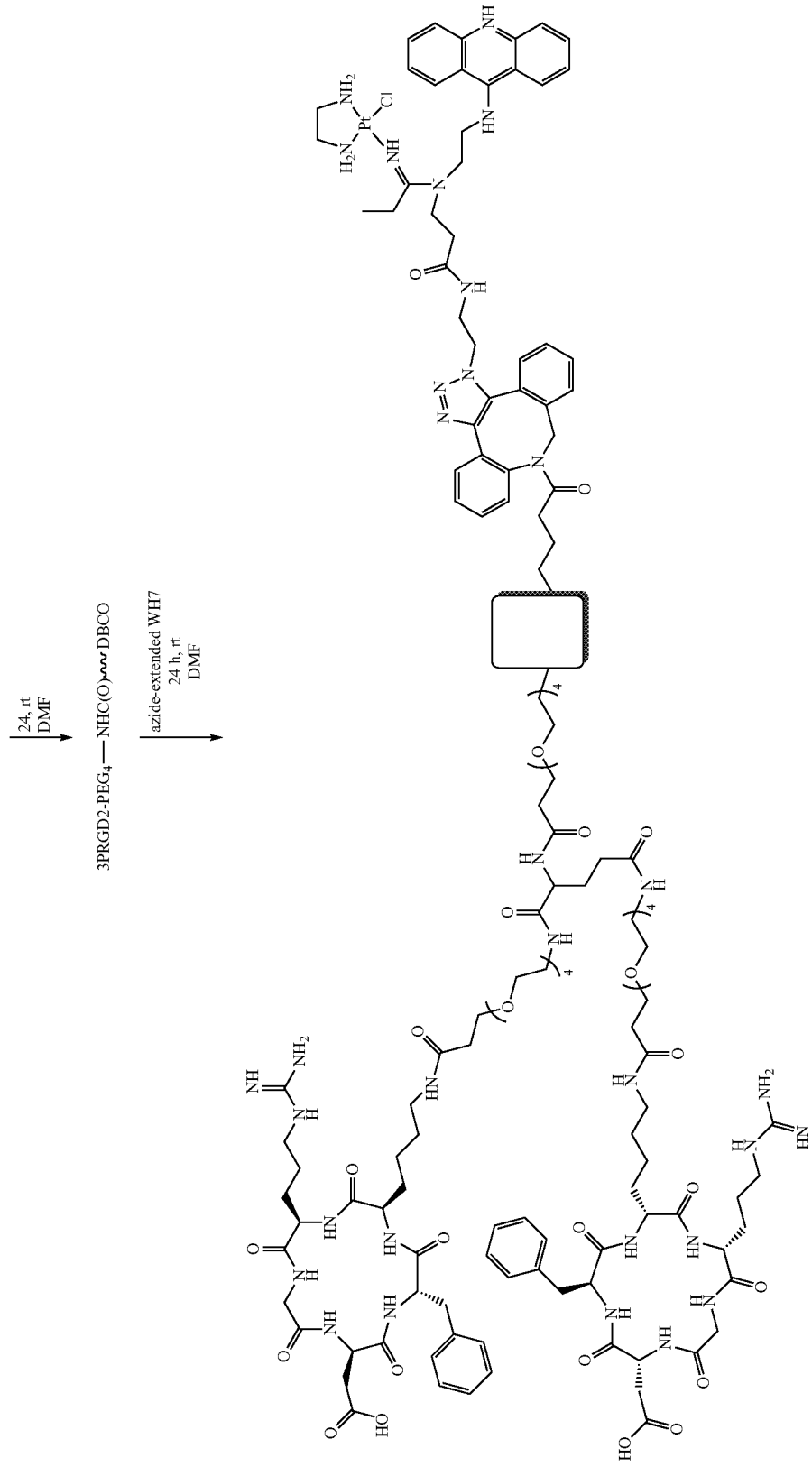

As explained above, the method of conjugating is applicable to various types of the biologically active moiety such as a small molecule, a receptor-targeted vector, a nanoparticle and a polymer. The method generally includes reacting the terminal functional group of E with a counterpart functional group of the biologically active moiety. In some embodiments, the counterpart functional group is selected from the group consisting of a thiol, an amino, a strained alkyne and a azido group.

Some embodiments provided herein are antibody-payload (or antibody-drug) conjugates comprising: (a) an antibody moiety that (e.g., a monoclonal antibody) or an antigen-binding fragment thereof that specifically binds to a target; (b) one or more drug moieties, each drug moiety being a cytotoxic agent; and (c) a linker; wherein the cytotoxic agent is conjugated to the antibody moiety via the linker. The term "conjugated" as used in this disclosure shall mean covalently bound, which can be directly or via an intervening covalently bound structure.

In certain embodiments, the antibody-drug conjugate provided herein has a molar ratio of the antibody moiety to the drug moiety that is between 1:1 and 1:20. In specific embodiments, the antibody-drug conjugate provided herein has a molar ratio of the antibody moiety to the drug moiety that is between 1:1 and 1:15. In specific embodiments, the antibody-drug conjugate provided herein has a molar ratio of the antibody moiety to the drug moiety that is between 1:1 and 1:12. In specific embodiments, the antibody-drug conjugate provided herein has a molar ratio of the antibody moiety to the drug moiety that is between 1:1 and 1:8. In preferred embodiments, the antibody-drug conjugate provided herein has a molar ratio of the antibody moiety to the drug moiety that is between 1:3 and 1:5. In a specific embodiment, the antibody-drug conjugate provided herein has a molar ratio of the antibody moiety to the drug moiety that is 1:3. In another specific embodiment, the antibody-drug conjugate provided herein has a molar ratio of the antibody moiety to the drug moiety that is 1:4. In another specific embodiment, the antibody-drug conjugate provided herein has a molar ratio of the antibody moiety to the drug moiety that is 1:5.

The drug moiety is conjugated to one or more chains of the antibody moiety. In some embodiments, the drug moiety is conjugated to one chain of the antibody moiety (for example, when the antibody moiety is a single-chain Fvs (scFv), or when the antibody moiety is a multi-chain antibody, such as an immunoglobulin (which is a tetramer), or antigen-binding fragment thereof). In other embodiments, the drug moiety is conjugated to two or more chains of the antibody moiety (when the antibody moiety is a multi-chain antibody, such as an immunoglobulin, or antigen-binding fragment thereof). In a specific embodiment, the drug moiety is conjugated to two identical chains of an immunoglobulin, e.g., the heavy chains or the light chains. In other embodiments, the drug moiety is conjugated to all chains of the antibody moiety (when the antibody moiety is a multi-chain antibody, such as an immunoglobulin or antigen-binding fragment thereof).

In a specific embodiment, the drug moiety is conjugated to one or more sites in the constant region of an antibody. In a particular embodiment, the drug moiety is conjugated to the Fc region of an antibody that is an immunoglobulin.

Another aspect of the invention provides a method of treating cancer, comprising administering to a subject in need a therapeutically effective amount of the payload, conjugate, pharmaceutically salt thereof, or pharmaceutical composition described herein. The therapeutically effective amount required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated.

The target cancers include mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumors, primary or secondary brain tumors, Hodgkin's disease, chronic or acute leukemias, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, and retinoblastoma.

The exact formulation, route of administration and dosage for the pharmaceutical compositions can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

The compounds and complexes described in this patent document are further illustrated by the examples below. These examples serve only to illustrate the invention and should not be interpreted as limiting the scope of the invention in any way, since further modifications encompassed by the disclosed invention will be apparent to those skilled in the art. All such modifications are deemed to be within the scope of the invention as defined in the present specification and claims.

EXAMPLES

The following non-limiting examples further illustrate certain aspects of the present invention.

Example 1. Preparation of PL1 and PL2

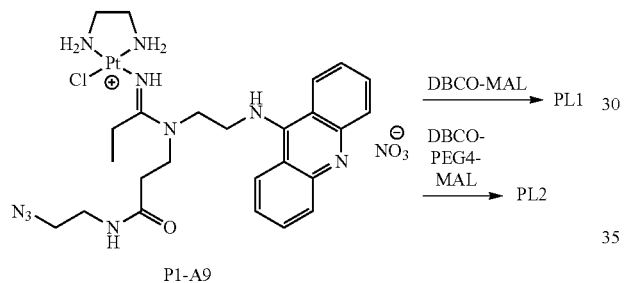

Both payloads were synthesized from AZIDO-AMINE-extended WH7 (compound P1-A9) and the appropriate DBCO derivative using copper-free click chemistry. Procedure for PL2: Stock solutions of P1-A9 and DBCO-PEG4-MAL (40 mM) were prepared in anhydrous DMF. 100 μL of the solution containing P1-A9 were combined with 100 μL of the DBCO-PEG4-MAL solution and the mixture was stored at room temperature for 24 h in the dark. The reaction was monitored, and complete/stoichiometric conversion confirmed, by LC-ESI-MS (reverse-phase C18, gradient used: mobile phase A: H2O, B: methanol. 0~5 mins, 5% B; 5~20 mins, increasing from 5% B to 95% B; 20~30 mins, 95% B; positive-ion mode MS). Pure conjugate free of unreacted precursors can be generated by carefully readjusting the ratio of the reactants if either of the two components was applied in excess. Characterization of the final product was based on mass spectrometric data (m/z for z=1, 2).

Example 2. Synthesis and ESI-ToF Analysis of Bioconjugates with Human Serum Albumin (HSA)

Conjugation reactions with HSA and platinum complex were performed in various buffers. The optimal reaction buffer was 10 mM Tris-HCl (pH 7.00), which was supplemented with 0.9% NaCl to avoid the loss of chloride on platinum complex and undesired side reactions. Incubations for 3 hours at room temperature gave conversion yields of 85-90% (Ellman's test). In a typical incubation procedure, 100 μL of HSA solution (100 mg/mL, 1.5 mM) and 9 μL of PL2 (20 mM) in DMF (1:1.2 molar ratio, i.e., 20% excess of PL2) were combined followed by dilution to a total volume of 500 μL using buffer. Mixtures were incubated for 3 hours at room temperature in the dark. Samples for ESI-ToF MS analysis were subjected to buffer exchange (ammonium bicarbonate) on P6 size-exclusion chromatography spin columns. Conjugates were stored in buffered solution at −20° C. or as lyophilized powder.

Example 3. Payloads Containing pH-Sensitive Linkers

Ketone-modified platinum-acridines were introduced as warheads in payloads via conversion into hydrazide groups. Hydrazide linkers were cleaved in the acidic environment of the lysosomes to release the active warhead.

Specifically, WH4 was reacted with 4-azidobutanehydrazide (AZIDO-HYDRAZIDE) to prepare the PA warhead for copper-free coupling chemistry with DBCO-PEG4-MAL, giving PL3. This new derivative was synthesized according to a reported method:

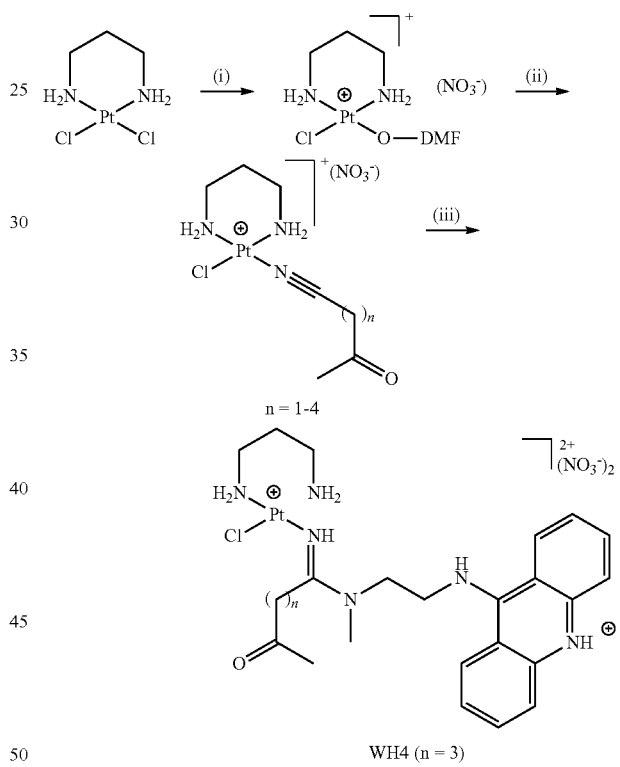

(i) AgNO3/DMF; (ii) oxoalkane nitrile derivative/DMF/50° C.; (iii) 1. N1-(acridin-9-yl)-N2-methylethane-1,2-diamine/DMF/rt; 2. 1 eq. HNO3/MeOH.

Extension of WH4. To 50 mg (69 μmol) of WH4 in 5 mL of methanol were added 50 mg (0.39 mmol) of 4-azidobutanehydrazide. The mixture was refluxed for 50 minutes. Several drops of glacial acetic acid were added to the mixture. After the mixture was heated for another 30 minutes, the reaction showed complete conversion by direct-injection ESI MS. The solvent was removed by rotary evaporation until the solution turned cloudy. It was then poured into 50 mL of vigorously stirred diethyl ether. After stirring for 2 hours the mixture was stored at 4° C. for 24 hours. The precipitate was recovered by filtration and washed with cold diethyl ether. Yield: 58 mg (94%) of a bright yellow microcrystalline solid. Characterization by NMR, ESI MS.

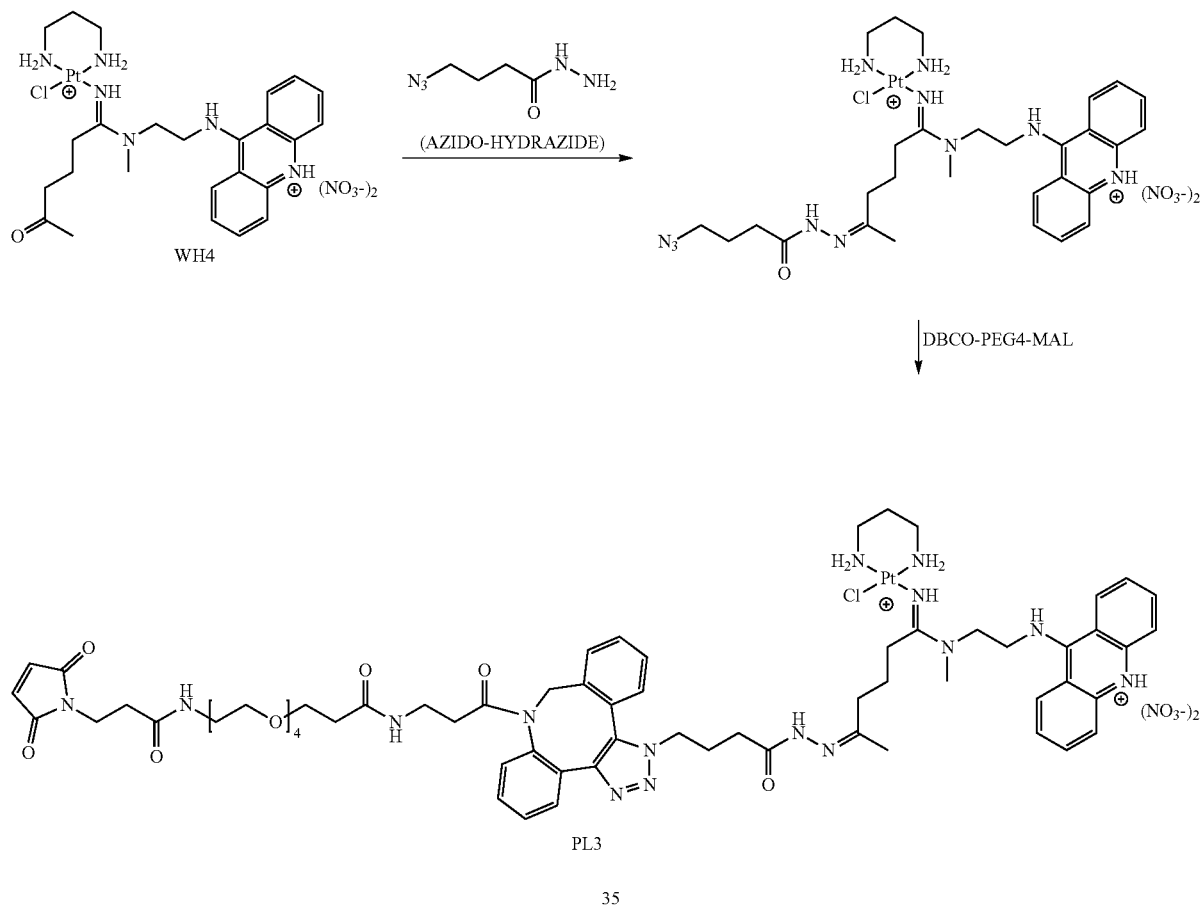
Example 4. Payloads Containing Cleavable Esters
Using the previously developed molecules WH1 and WH1-SUCC, the terminal carboxylic acid was extended with 2-azidoethan-1-amine (AZIDO-AMINE) and the newly introduced azide function can then be extended with DBCO-PEG4-MAL to generate PL4.
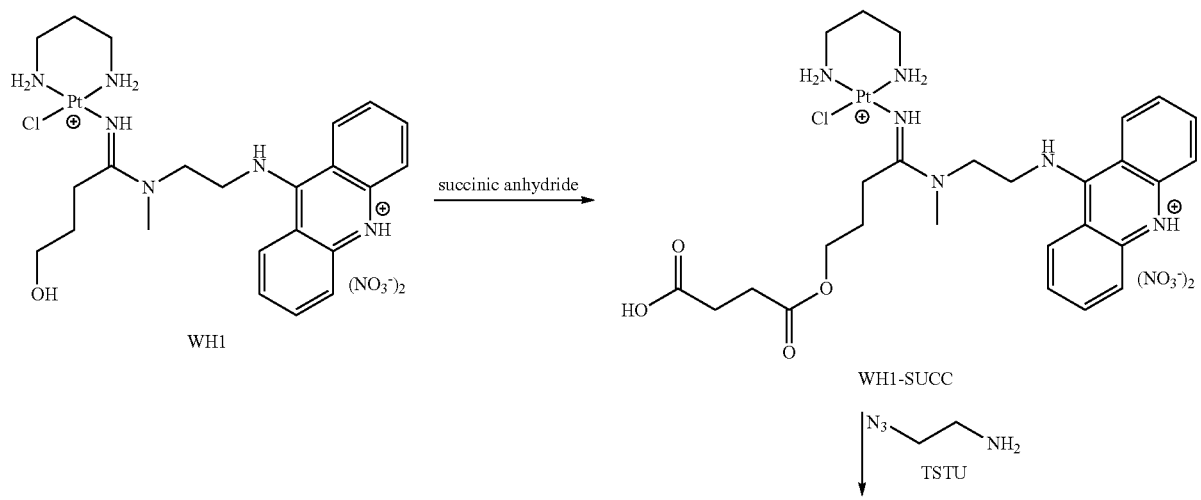

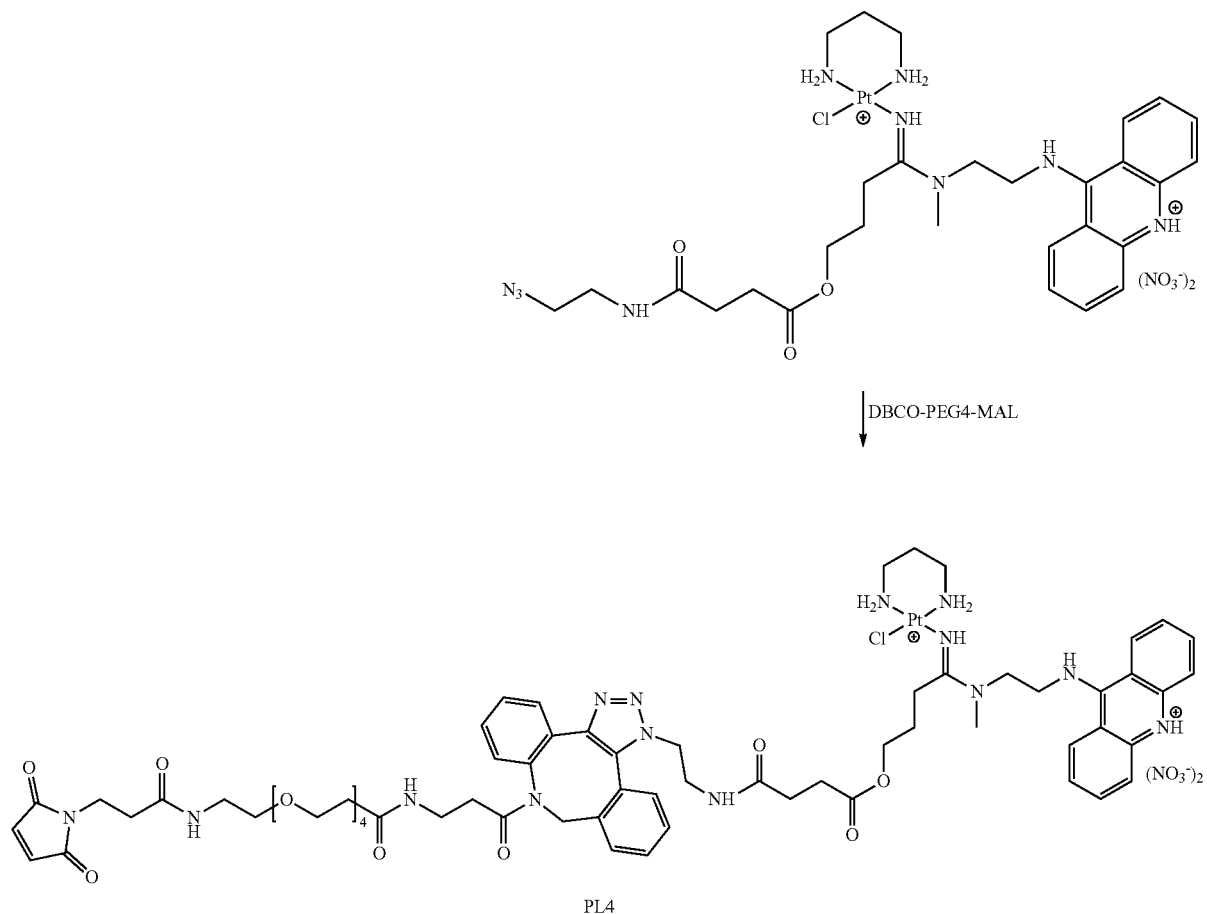

PL4

Example 5. Regioselective Conjugation of the Payload with Protein

A critical factor which determines the stability and biological activity of platinum-based pharmaceuticals is the reactivity of the leaving groups. Prior to the assembly of the payloads, the stability of payload/compound F-1 in buffers relevant to the preparation of the bioconjugates and their proposed application was examined. Compound F-1 is resistant to aquation and stable over a wide pH range, particularly in media containing physiological chloride (see the ESI). The extended conjugates F-2 and F-3 contain a platinum(II) center and a maleimide group, which are both electrophilic moieties and reactive with cysteine thiol. Binding of the metal with cysteine would be undesired because it would lead to irreversible sequestration of the cytotoxic compound by the carrier protein. Reaction of compound F-1 with GSH at neutral pH resulted in the substitution of the chloro leaving group by the nucleophilic cysteine sulfur, yielding mononuclear and thiolato-bridged adducts, a reactivity pattern previously observed in platinum-acridine agents and clinical platinum drugs (see the ESI). By contrast, when payloads F-2 and F-3 were incubated with GSH under the same conditions, selective and rapid (the reaction is complete in less than 1 h at 25° C.) Michael addition at the maleimide group was observed (see the ESI). These results suggest that platinum in F-2 and F-3 does not compete with cysteine-maleimide addition, which is a prerequisite for the desired application.

Synthesis of Maleimide-Modified Platinum-Acridine Payloads from Azide-Modified Derivative F-1.

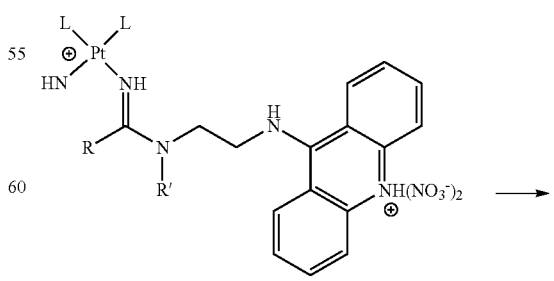

F-1: $L_2$ = en; R = Et;
R' = $(CH_2)_2C(O)NH(CH_2)_2N_3$

-continued

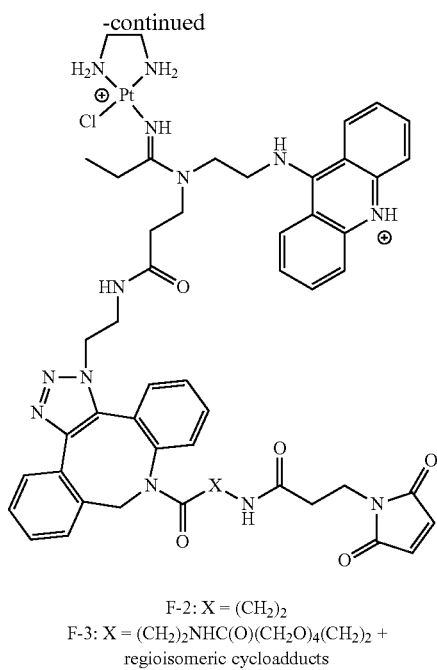

F-2: X = (CH$_2$)$_2$
F-3: X = (CH$_2$)$_2$NHC(O)(CH$_2$O)$_4$(CH$_2$)$_2$ +
regioisomeric cycloadducts Reagents and conditions: DBCO-maleimide (for F-2) DBCO-PEG4-maleimide (for F-3), DMF, rt, 16 h.

To investigate the bioconjugation chemistry, gel-purified, pharmaceutical-grade rHSA was chosen as a carrier protein and model for other serum proteins amenable to maleimide-thiol Michael addition. This includes immunoglobulin G-type (IgG) antibodies after selective reduction of inter-chain disulfide to free thiol groups. Ellman's test performed on rHSA treated with F-2 and F-3 confirmed that 85-90% of the free C34 present in the sample was modified with payload after incubation for 3 hours at room temperature. Unmodified rHSA and the size-exclusion chromatography (SEC)-purified conjugates rHSA-F-2 and rHSA-F-3 were also characterized by electrospray ionization time-of-flight mass spectrometry (ESI-ToF). The deconvoluted intact-protein masses obtained are in agreement with maleimide addition to C34 in both cases. Circular dichroism (CD) spectra recorded for rHSA and rHSA-F-3 suggest that maleimide addition occurs without perturbation of protein conformation (see the ESI).

Using the $^{15}$N-labeled payload F-3' (generated from the corresponding isotopically labeled platinum-acridine derivative, F-1') in conjunction with 2-D $^1$H-$^{15}$N heteronuclear single quantum coherence (HSQC) NMR spectroscopy, the regio selectivity of the bioconjugation reaction was confirmed. This spectroscopic tool takes advantage of the fact that the $^{15}$N chemical shifts of the [$^{15}$N]-ethane-1,2-diamine ([$^{15}$N]-en) nonleaving group are highly sensitive to changes in the Pt coordination sphere. Two distinct cross peaks are observed in the HSQC spectrum of rHSA-F-3' at δ($^{15}$N) −32.05 and −27.22, as expected for [$^{15}$N]-en coordination trans to Cl and N. This result firmly rules out the possibility of substitution of the chlorido ligand by the thiol group of C34, despite the fact that it is significantly more basic (pKa≈7) and nucleophilic than the cysteine in GSH. This undesired reactivity would have resulted in a pronounced deshielding of the $^{15}$N nucleus trans to S and a downfield shift of the corresponding cross peak in the $^{15}$N dimension, as demonstrated for the GSH adducts formed by compound F-1'. 2-D HSQC NMR spectra recorded over one week were unchanged, demonstrating that rHSA-F-3' is stable in physiological chloride-supplemented media, which suppresses aquation and other potential secondary reactions of platinum.

To further corroborate the structural integrity of the payload in rHSA-F-3 and the site-specificity of the maleimide conjugation, tryptic digests of the bioconjugate were analyzed by liquid chromatography-high-resolution mass spectrometry (LC-HRMS) and tandem MS. Proteolytic digestion of rHSA-F-3 had to be performed without prior reduction of the 17 disulfide bonds of the protein with 1,4-dithiothreitol (DTT) or tris(tricarboxyethyl)phosphine (TCEP) as the monochlorido-Pt(II) moiety in F-1 readily reacts with these agents. Likewise, exposure of the digest to ammonium bicarbonate had to be minimized due to the inherent instability of Pt—Cl groups in this buffer. Proteolytic digestion of rHSA and rHSA-F-3 generates a 21-amino acid fragment, ALVLIAFAQYLQQCPFEDHVK (residues 21-41, where the single free cysteine, C34, is highlighted in bold), which is located within the N-terminal domain (IA) of the protein. MS/MS spectra recorded of this sequence generated from rHSA-F-3 unequivocally demonstrate that payload F-3 is covalently attached to C34 through the maleimide group. Treatment of rHSA-F-3 with thiourea (tu), which readily replaces the chloride leaving group in platinum-acridines without reversing Pt—N and Pt—S bonds, and MS/MS analysis of the fragments after tryptic digestion of the modified protein further confirms the presence of an intact payload.

Finally, the fluorescent properties of the 9-aminoacridine chromophore was utilized to study the uptake of rHSA-F-3 and compound F-1 into SK-MEL-2 melanoma cells. The cell line was chosen because it expresses relatively low levels of cation transporters (CellMiner Analysis Tool, NCI; https://discover.nci.nih.gov/cellminer), which are involved in delivering cationic platinum drugs across the cell membrane. The goal was to assess if an HSA-mediated endocytic pathway might exist for platinum-acridines and if this pathway would have an advantage over ion-transporter-mediated uptake. Confocal microscopy images of SK-MEL-2 cells treated with rHSA-F-3 for 4 h show bright blue fluorescence associated with the cell membrane and distinct cytoplasmic vesicles, some of which colocalize with fluorescently stained acidified lysosomes. Under the same conditions, compound F-1 produces a significantly weaker paracellular fluorescence. These observations are in agreement with more efficient internalization of platinum-acridine when attached to rHSA by endocytic vesicular transport.

This study confirmed the generation of the first bioconjugate of a cytotoxic Pt(II)-based agent containing a reactive chloride leaving group. Current HSA-based delivery platforms for cisplatin-type agents in (pre)clinical development take advantage of inert Pt(IV) prodrug payloads to overcome the inherent and undesired reactivity of platinum with nucleophilic amino acid residues. The system demonstrates that payload stability can also be achieved for Pt(II) if cysteine is site-specifically modified by maleimide conjugation and by introducing suitable spacers that prevent secondary reactions of the metal with other nucleophilic protein residues. In this regard, the DBCO-maleimide linker modules introduced in payloads F-2 and F-3 appear to promote the necessary selectivity and stability. The high selectivity of the bioconjugation reaction can be attributed to the fact that chloride substitution in platinum-acridines by cysteine sulfur proceeds significantly slower ($t_{1/2}$≈180 min. at 25° C., pH 7.2) than the Michael addition. This contrasts the promiscuous reactivity of cisplatin with serum albumin, which leads to nonspecific adducts with solvent-accessible methionine, histidine, and cysteine (C34) residues. In this study a non-cleavable linker was incorporated into the payloads to facilitate characterization of the conjugates under conditions that might lead to linker cleavage. Release of the cytotoxic platinum-acridine warhead in rHSA-F-2 and rHSH-F-3 would require complete lysosomal degradation of the bioconjugate. ADC technology has devised linker designs that allow stimuli-responsive or enzyme-triggered release of a cytotoxic warhead in cancer cells. Incorporation of platinum-compatible cleavable linkers instead of a non-cleavable surrogate will allow controlled release of platinum-acridine agents to harness their nanomolar cell kill potential. The high potency at low-nanomolar inhibitory concentrations observed in several NCI-60 cancer models rivals that of other DNA-targeted ADC warheads, such as the topoisomerase poison SN-38. Their unique spectrum of activity and their synthetic versatility and chemical robustness makes platinum-acridines attractive candidates for delivery as antigen-targeted drug conjugates.

While this invention has been described with an emphasis upon preferred embodiments, it will be obvious to those of ordinary skill in the art that variations in the preferred compositions and methods can be used and that it is intended that the invention can be practiced otherwise than as specifically described herein. Accordingly, this invention includes all modifications encompassed within the spirit and scope of the invention as defined by the claims that follow.

The invention claimed is:

1. A compound of formula E-A-F, wherein:
F is represented with the following general formula:

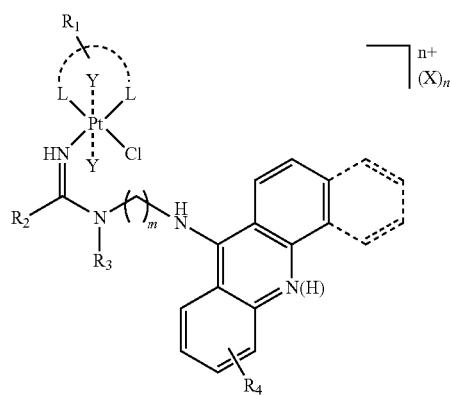

wherein
$R_1$ represents an optional substituent of L and is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, (mono-, di-, or trihalogeno)methyl, and $C_{1-10}$ alkoxy;
$R_2$ and $R_3$ each independently represents a $C_{1-10}$ alkyl, wherein the $C_{1-10}$ alkyl is optionally
(a) intercepted with one or more structural moieties selected from the group consisting of amino, oxygen, sulfur, amide, ester, carbamate, sulfonamide, sulfonyl, carbonate, ketone, disulfide, $(CH_2CH_2O)_p$ wherein p is an integer of 1 to 10, aryl or 5 to 12 membered aromatic or non-aromatic heterocyclic group; or
(b) substituted with one or more structural moieties selected from the group consisting of hydroxy, imino, oxo, cyano, $C_{1-10}$ alkoxy, $C_{1-10}$ alkylthio, $C_{1-6}$ alkylsulfonyl, di-$C_{1-10}$ alkylamine, aryl or 5 to 12 membered aromatic or non-aromatic heterocyclic group;
$R_4$ is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, or (mono-, di-, or trihalogeno)methyl;
each L represents monodentate $NH_3$ or an amine ligand wherein the nitrogen coordinates to Pt, further wherein the two amine ligands optionally link up to form a diamine ligand (chelate);
X is nitrate or halide;
Y is an optional ligand, wherein when Y is present, Pt is Pt(IV), and when Y is void, Pt is Pt(II), and A contains a triazole formed from the reaction between a strained alkyne and an azido group;
A is a linkage comprising one or more structural moieties selected from the group consisting of ester, amide, amino, carbamate, hydrazide, triazole, and disulfide, and A links E to one of $R_2$ and $R_3$;
E is a linker comprising a free terminal functional group, wherein the terminal functional group is an electrophilic group or is selected from the group consisting of a strained alkyne, an azido group ($—N_3$) and a hydrazine group;
m is 1, 2, 3, 4, 5 or 5; and
n is 1, 2, 3 or 4.

2. The compound of claim 1, wherein E further comprises $C_{1-10}$ alkyl, wherein the $C_{1-10}$ alkyl is optionally
(a) intercepted with one or more structural moieties selected from the group consisting of amino, oxygen, sulfur, amide, ester, carbamate, sulfonamide, sulfonyl, carbonate, ketone, disulfide, $(CH_2CH_2O)_p$ wherein p is an integer of 1 to 10, aryl or 5 to 12 membered aromatic or non-aromatic heterocyclic group; or
(b) substituted with one or more structural moieties selected from the group consisting of hydroxy, imino, oxo, cyano, $C_{1-10}$ alkoxy, $C_{1-10}$ alkylthio, $C_{1-6}$ alkylsulfonyl, di-$C_{1-10}$ alkylamine, aryl or 5 to 12 membered aromatic or non-aromatic heterocyclic group.

3. The compound of claim 1, wherein the terminal functional group of E is selected from the group consisting of

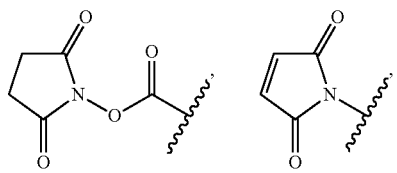 [SMILES: *C(=O)ON1C(=O)CCC1=O ; *N1C(=O)C=CC1=O]

a haloacetamide, a strained alkyne, an azido group ($—N_3$) and a hydrazine group.

4. The compound of claim 1, wherein Pt is Pt(IV), and the terminal functional group of E is

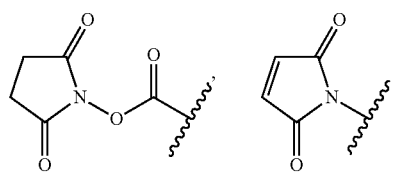 [SMILES: *C(=O)ON1C(=O)CCC1=O ; *N1C(=O)C=CC1=O]

or haloacetamide.

5. The compound of claim 1, wherein A contains a group cleavable via enzymatic dipeptide cleavage, pH-sensitive cleavage, platinum-mediated hydrolytic ester cleavage, or self-immolative linker degradation.

6. The compound of claim 1, wherein A contains one or more structural moieties selected from the group consisting of

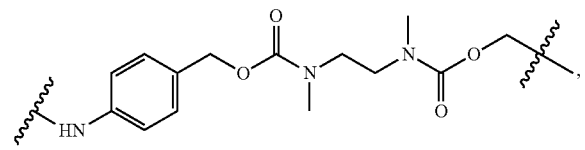,

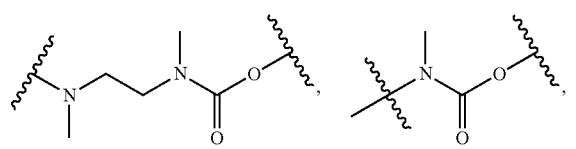,

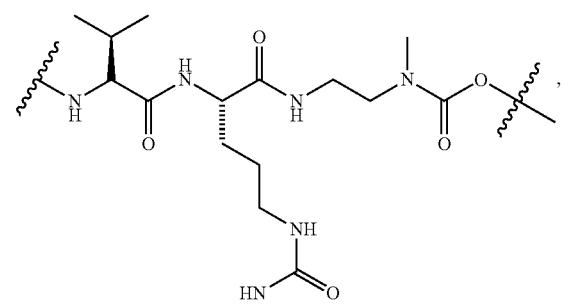,

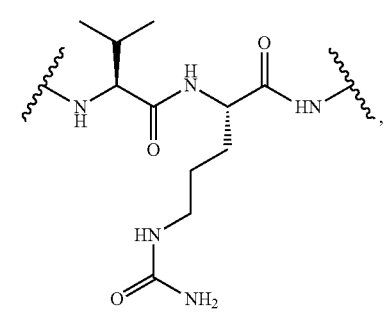,

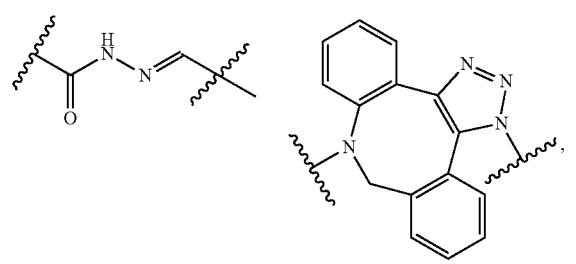,

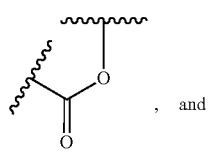, and

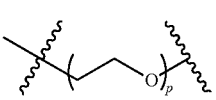

wherein p is 1-10.

7. The compound of claim 1, wherein Pt is Pt(IV), A contains a triazole and a cleavable group.

8. The compound of claim 1, wherein Pt is Pt(IV), wherein n is 1 or 2.

9. The compound of claim 1, wherein Pt is Pt(IV), wherein m is 1 or 2.

10. The compound of claim 1, wherein Pt is Pt(IV), wherein the two L ligands linked up to form a ligand selected from the group consisting of 1,2-diaminoethane, 1,3-diamino-propane,

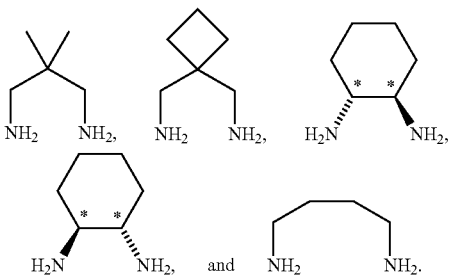

11. The compound of claim 1, wherein Y is present, and Pt is Pt(IV).

12. The compound of claim 1, Y is Cl, Pt is Pt(IV), and the two L ligands link together to form 1,3-diamino-propane.

13. The compound of claim 1, wherein F is represented as

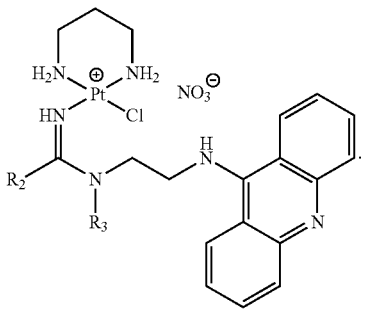.

14. The compound of claim 1, which is selected from the group consisting of

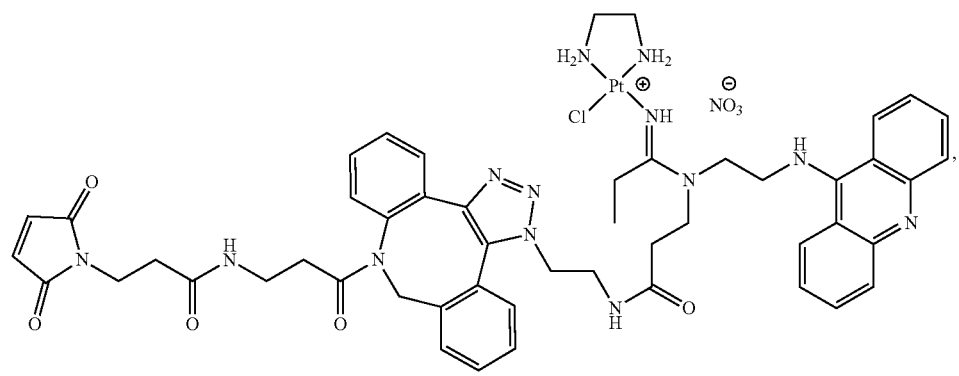
PL1
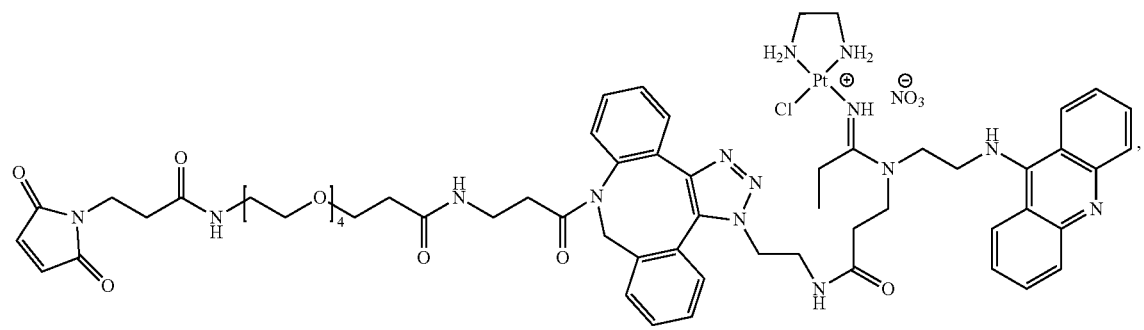
PL2
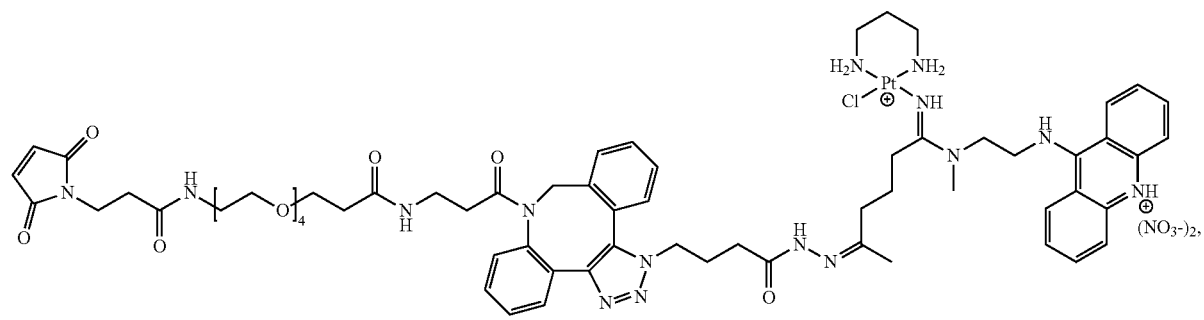
PL3
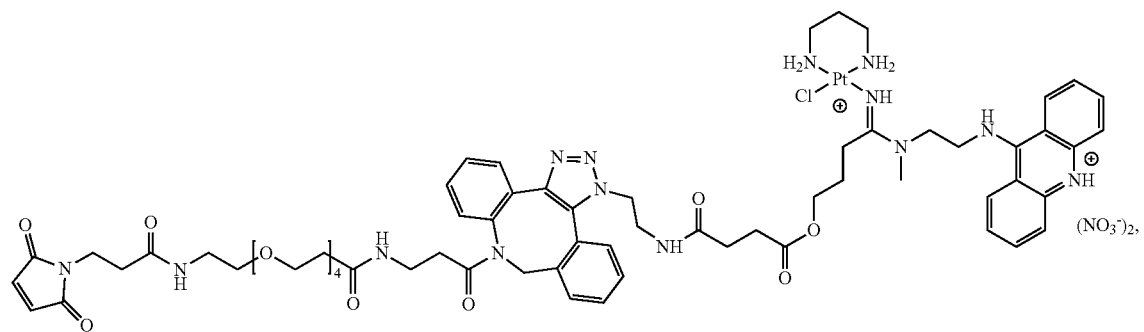
PL4

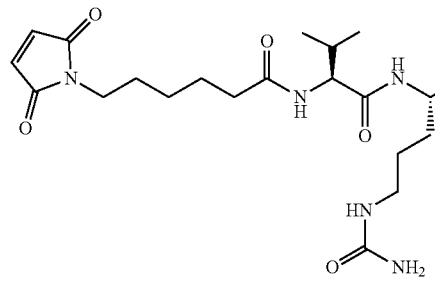
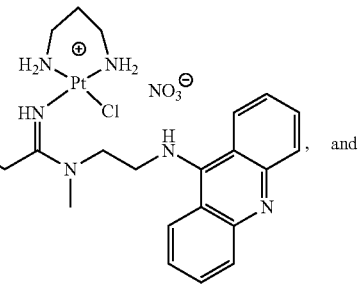

PL5

, and

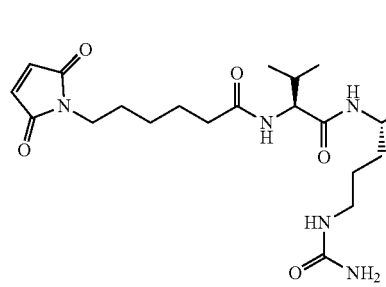
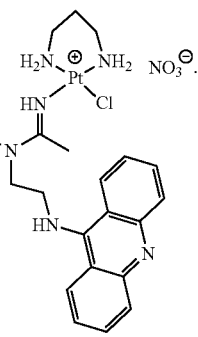

PL6

.

15. A conjugate of a biologically active moiety and the compound of claim 1, wherein the biologically active moiety is selected from the group consisting of carbohydrate, peptide, folic acid, kinase inhibitor, (growth) hormone-receptor antagonist, micelle- and liposome-forming lipid, proapoptotic agent, chemosensitizing agent, a receptor-targeted vector, nanoparticle and polymer.

16. The compound of claim 1, wherein Y is Cl—, OH—, CH3COO—, or $R_a$COO—, wherein $R_a$ an alkyl.

17. The compound of claim 1, wherein one of R2 and R3 comprises an ester moiety.

18. The compound of claim 17, wherein the other of R2 and R3 is a $C_{1-6}$ alkyl.

19. The compound of claim 17, wherein the other of R2 and R3 is methyl.

20. The compound of claim 1, wherein the two L ligands linked up to form 1,3-diamino-propane.

21. The compound of claim 4, wherein A links E to $R_2$ and contains

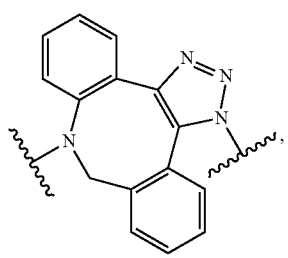, 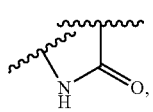

-continued

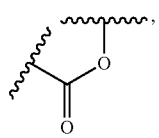, and 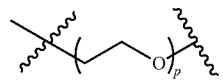

wherein p is 1-10.

22. The compound of claim 21, wherein the terminal functional group of E is

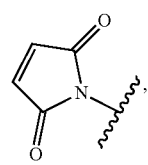

and the two L ligands linked up to form a ligand selected from the group consisting of 1,2-diaminoethane, 1,3-diamino-propane,

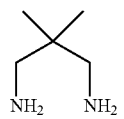 and 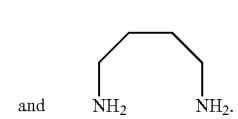.

23. The compound of claim 1, wherein Pt is Pt(IV), and the compound is derived from a Pt(II) compound selected from the group consisting of PL3
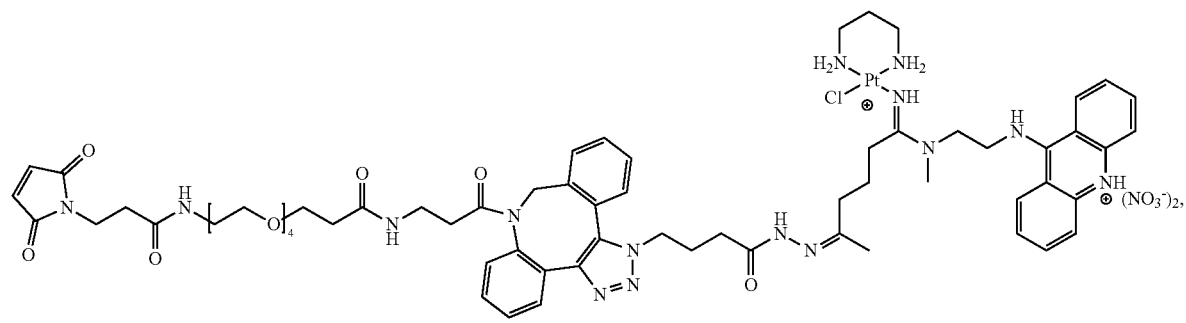
PL4
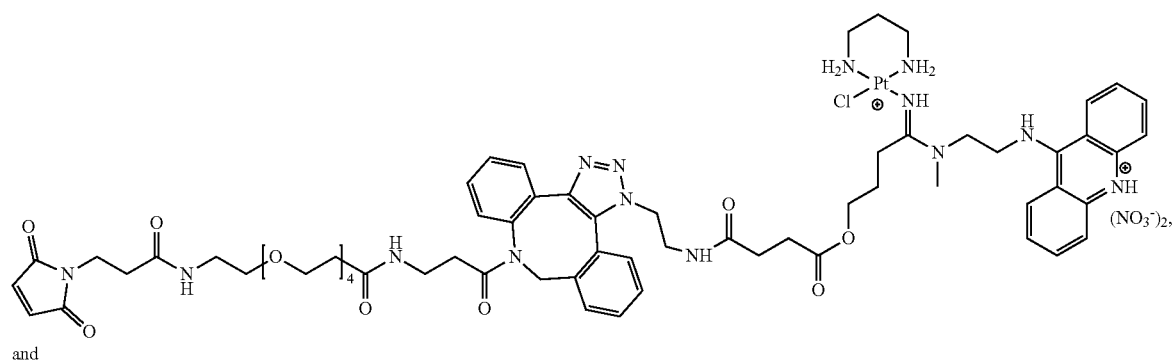
and
PL5
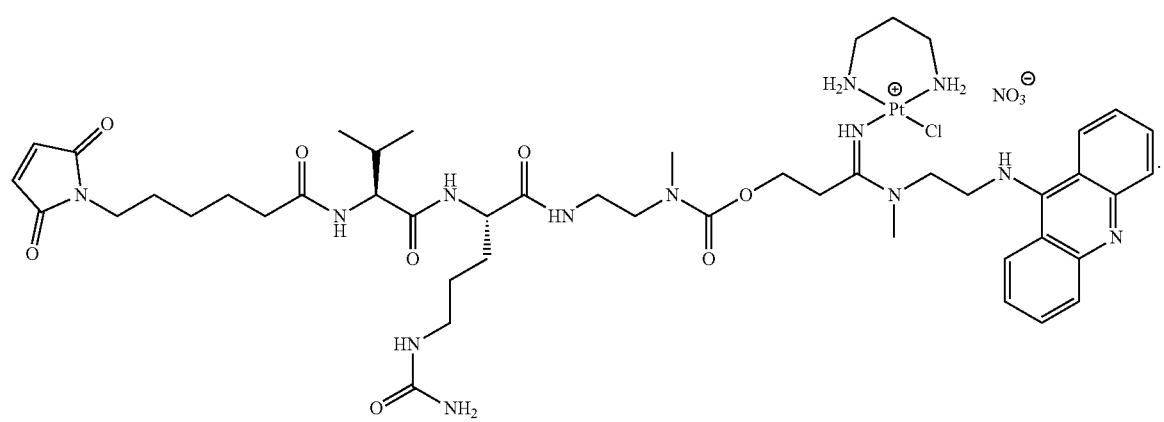
* * * * *